United States Patent
Uvaydov et al.

(10) Patent No.: US 11,969,266 B2
(45) Date of Patent: Apr. 30, 2024

(54) EMBEDDED NETWORKED DEEP LEARNING FOR IMPLANTED MEDICAL DEVICES

(71) Applicant: Northeastern University, Boston, MA (US)

(72) Inventors: Daniel Uvaydov, Allston, MA (US); Raffaele Guida, Boston, MA (US); Francesco Restuccia, Boston, MA (US); Tommaso Melodia, Newton, MA (US)

(73) Assignee: Northeastern University, Boston, MA (US)

( * ) Notice: Subject to any disclaimer, the term of this patent is extended or adjusted under 35 U.S.C. 154(b) by 357 days.

(21) Appl. No.: 17/176,229

(22) Filed: Feb. 16, 2021

(65) Prior Publication Data

US 2021/0259639 A1    Aug. 26, 2021

Related U.S. Application Data

(60) Provisional application No. 62/976,518, filed on Feb. 14, 2020.

(51) Int. Cl.
*A61B 5/00*       (2006.01)
*G06N 3/04*      (2023.01)
(Continued)

(52) U.S. Cl.
CPC .......... *A61B 5/7267* (2013.01); *A61B 5/6867* (2013.01); *A61B 5/7225* (2013.01);
(Continued)

(58) Field of Classification Search
CPC ........................... G16H 50/20; A61B 2503/06
(Continued)

(56) References Cited

U.S. PATENT DOCUMENTS

2006/0238386 A1* 10/2006 Huang ................. G10L 19/008
                                                              704/E19.044
2008/0091115 A1*  4/2008 Popov ..................... A61B 7/04
                                                              600/528

(Continued)

OTHER PUBLICATIONS

Alhussein et al., "Cognitive iot-cloud integration for smart healthcare: Case study for epileptic seizure detection and monitoring," Mobile Networks and Applications, vol. 23, No. 6, pp. 1624-1635, 2018.

(Continued)

*Primary Examiner* — Fabricio R Murillo Garcia
(74) *Attorney, Agent, or Firm* — Verrill Dana, LLP

(57) ABSTRACT

A deep learning medical device implantable in a body is provided. The device includes a processing and communication unit and a sensing and actuation unit. The processing and communication unit includes a deep learning module including a neural network trained to process the input samples, received from the sensing and actuation unit, through a plurality of layers to classify physiological parameters and provide classification results. A communication interface in communication with the deep learning module receives the classification results for ultrasonic transmission through biological tissue. Methods of sensing and classifying physiological parameters of a body and methods of embedding deep learning into an implantable medical device are also provided.

19 Claims, 14 Drawing Sheets

(51) Int. Cl.
*G06N 3/08* (2023.01)
*G16H 40/60* (2018.01)
(52) U.S. Cl.
CPC ............... *A61B 5/74* (2013.01); *G06N 3/04* (2013.01); *G06N 3/08* (2013.01); *G16H 40/60* (2018.01)
(58) Field of Classification Search
USPC .................................................. 340/539.12
See application file for complete search history.

(56) References Cited

U.S. PATENT DOCUMENTS

| | | | | |
|---|---|---|---|---|
| 2009/0234608 | A1* | 9/2009 | Fujiwara | G06J 1/00 702/85 |
| 2011/0160549 | A1* | 6/2011 | Saroka | A61B 5/05 343/700 R |
| 2012/0254100 | A1* | 10/2012 | Grokop | A61B 5/1123 706/52 |
| 2012/0311171 | A1* | 12/2012 | Holley | H04N 21/2401 709/231 |
| 2016/0286267 | A1* | 9/2016 | Tang | H04N 21/4782 |
| 2017/0231568 | A1* | 8/2017 | An | A61B 5/4836 600/301 |
| 2017/0332979 | A1* | 11/2017 | Nagisetty | A61B 5/7203 |
| 2018/0027077 | A1 | 1/2018 | Melodia et al. | |
| 2018/0220305 | A1* | 8/2018 | Lei | H04L 5/0053 |
| 2018/0299491 | A1* | 10/2018 | Holaday | G01R 13/34 |
| 2019/0313908 | A1 | 10/2019 | Melodia et al. | |
| 2020/0050964 | A1* | 2/2020 | Vassilev | G06F 18/24 |
| 2021/0106281 | A1* | 4/2021 | Tran | A61B 5/486 |
| 2021/0251574 | A1* | 8/2021 | Halter | A61B 5/726 |

OTHER PUBLICATIONS

Lyu et al., "Intracranial electrodes monitoring improves seizure control and complication outcomes for patients with temporal lobe epilepsy a retrospective cohort study," International Journal of Surgery, vol. 51, pp. 174-179, 2018.

Wang et al., "A Low Power Cardiovascular Healthcare System with Cross-layer Optimization from Sensing Patch to Cloud Platform," IEEE transactions on biomedical circuits and systems, 2019, pp. 314-329.

Santagati et al., "An Implantable Low-Power Ultrasonic Platform for the Internet of Medical Things," in Proc. of IEEE Conf. on Computer Communications (INFOCOM), Atlanta, USA, May 2017, 9 pages.

Galluccio et al., "Challenges and Implications of Using Ultrasonic Communications in Intra-Body Area Networks," in EEE Annual Conf. on Wireless On-demand Network Systems and Services (WONS), 2012, pp. 182-189.

Santagati et al., "A Software-Defined Ultrasonic Networking Framework for Wearable Devices," IEEE/ACM Transactions on Networking, vol. PP, No. 99, pp. 1-14, 2016.

Ahmedt-Aristizabal et al., "Deep Classification of Epileptic Signals," in 2018 40th Annual International Conference of the IEEE Engineering in Medicine and Biology Society (EMBC). IEEE, 2018, pp. 332-335.

Acharya et al., "Deep Convolutional Neural Network for the Automated Detection and Diagnosis of Seizure Using EEG Signals," Computers in biology and medicine, vol. 100, pp. 270-278, 2017.

Yao et al., "Deeplot: Compressing Deep Neural Network Structures for Sensing Systems with a Compressor-Critic Framework," in Proceedings of the 15th ACM Conference on Embedded Network Sensor Systems. ACM, 2017, 14 pages.

Yao et al., "FastDeeplot: Towards Understanding and Optimizing Neural Network Execution Time on Mobile and Embedded Devices," in Proceedings of the 16th ACM Conference on Embedded Networked Sensor Systems. ACM, 2018, pp. 278-291.

Xue et al., "DeepFusion: A Deep Learning Framework for the Fusion of Heterogeneous Sensory Data," in Proceedings of the Twentieth ACM International Symposium on Mobile Ad Hoc Networking and Computing. ACM, 2019, pp. 151-160.

Yao et al., "Deepsense: A Unified Deep Learning Framework for Time-Series Mobile Sensing Data Processing," in Proceedings of the 26th International Conference on World Wide Web. International World Wide Web Conferences Steering Committee, 2017, pp. 351-360.

Faust et al., "Deep Learning for Healthcare Applications Based on Physiological Signals: A Review," Computer methods and programs in biomedicine, vol. 161, 32 pp. 2018.

Hussein et al., "Epileptic Seizure Detection: A Deep Learning Approach," arXiv preprint arXiv:1803.09848, 2018, 12 pages.

* cited by examiner

EMBEDDED NETWORKED DEEP LEARNING FOR IMPLANTED MEDICAL DEVICES

CROSS REFERENCE TO RELATED APPLICATIONS

This application claims priority under 35 U.S.C. § 119(e) of U.S. Provisional Application No. 62/976,518, filed on 14 Feb. 2020, entitled "Embedded Networked Deep Leaning for Implanted Medical Devices," the disclosure of which is hereby incorporated by reference.

STATEMENT REGARDING FEDERALLY SPONSORED RESEARCH OR DEVELOPMENT

This invention was made with government support under Grant Number 1618731 awarded by the National Science Foundation. The government has certain rights in the invention.

BACKGROUND

Early prediction and real-time response to life-threatening health events is becoming increasingly important. Research in the medical domain has shown that deep learning (DL)-based algorithms can come up with advanced diagnoses that are hardly achievable by doctors. Yet, these sophisticated inference techniques are confined to server-scale platforms, and thus unable to process data at its source, the human body.

Recent work has demonstrated that neural network structures can be compressed to improve their run-time performance, making them more suitable for IoT devices that have limited resources. However, these techniques focus on model compression only and do not address the broader challenges of bringing deep learning to the implantable medical device (IMD) domain.

Implantable medical devices include a plethora of miniaturized bioelectronic platforms, including neural dust nodes, neurostimulators, optogenetic stimulators, implantable sensors and actuators. Miniaturized implantable sensors can extract large amounts of data that require memory and fast processing capabilities. For instance, intracranial electroencephalograms (iEEGs) are characterized by sampling rates larger than 2 kHz. However, these devices are passive, can perform one-time operations, and have limited resources (e.g., size, computation, memory, and energy), not allowing for the computational and power resources necessary to run complex DL algorithms for sustained periods of time.

SUMMARY

The technology described herein relates to implantable medical devices with a deep learning core for the Internet of Implantable Medical Things (IoIMT). The technology, also termed embedded networked deep learning (ENDL) herein, implements a deep learning neural network such as a convolutional neural network (CNN) to classify health-related physiological signals and can perform early prediction of critical events, such as seizures and other abnormalities. To implement deep learning on an implantable device is challenging, because (i) the memory, computational and power resources are limited, and (ii) the components that need to interact with each other have different operating latencies, transfer data rates and clock domains. For these reasons the technology also provides a system model and a mathematical formulation to assist with the implementation. One exemplary practical implementation is based on hardware, such as a field programmable gate array (FPGA), as the core. Experimental results are also reported, which show the feasibility of device, specifically of the implementation of the CNN on an embedded system that includes a communication unit. The deep learning output was transferred through animal tissues to a receiving unit with a reported classification accuracy greater than 80% with 9 times less latency than a CPU and 4.5 times less energy than cloud based methods.

In some embodiments, a deep learning medical device implantable in a body is provided having a sensing and actuation unit and a processing and communication unit in communication with the sensing and actuation unit. The sensing and actuation unit comprises one or more implantable sensors operative to sense physiological parameters of a body and one or more actuators. The processing and communication unit comprises a deep learning module operative to receive input samples from the sensing and actuation unit. The deep learning module includes a neural network trained to process the input samples through a plurality of layers to classify the physiological parameters sensed by the sensing and actuation unit and provide classification results. The processing and communication unit also includes a communication interface in communication with the deep learning module to receive the classification results. The communication interface comprises an ultrasonic transceiver to transmit and receive ultrasonic signals through biological tissue to and from an external device. In some embodiments, the processing and communication unit can also determine instructions, based on the classification results, for the sensing and actuation unit and transmit the instructions to the sensing and actuation unit.

In some embodiments, a method of sensing and classifying physiological parameters of a body is provided. The method includes providing a deep learning medical device implantable in a body; transmitting input samples from the sensing and actuating unit to the communication and processing unit; classifying the input samples into classification results; and transmitting the classification results to the external device.

In some embodiments, a method of embedding deep learning into an implantable medical device is provided. The method includes training a deep learning module with a set of physiological data; embedding the deep learning module onto a processing and communication unit of an implantable medical device, the implantable medical device further comprising a sensing and actuation unit comprising one or more implantable sensors and one or more actuators in communication with the deep learning module; and a communication interface in communication with the processing and communication unit, the communication interface comprising an ultrasonic transceiver to transmit and receive ultrasonic signals through biological tissue to and from an external device.

Additional aspects, features, and embodiments of the technology include the following:

1. A deep learning medical device implantable in a body, comprising:
    a sensing and actuation unit comprising one or more implantable sensors operative to sense physiological parameters of a body and one or more actuators; and
    a processing and communication unit, in communication with the sensing and actuation unit, comprising:
        a deep learning module operative to receive input samples from the sensing and actuation unit, the deep learning module including a neural network trained to process the input samples through a plurality of layers to classify the physiological parameters sensed by the sensing and actuation unit and provide classification results, and a communication interface in communication with the deep learning module to receive the classification results, the communication interface comprising an ultrasonic transceiver to transmit and receive ultrasonic signals through biological tissue.

2. The device of 1, wherein the processing and communication unit comprises one or more logic devices, and the deep learning module is implemented in circuitry of the one or more logic devices.

3. The device of any of 1-2, wherein the one or more logic devices include one or more of a field programmable gate array (FPGA), application specific integrated circuit (ASIC), complex programmable logic device (CPLD), small-scale integrated circuit, programmable logic array, programmable logic device, and masked-programmed gate array.

4. The device of any of 1-3, wherein the processing and communication unit comprises one or more processors, and the deep learning module is implemented on the one or more processors.

5. The device of any of 1-4, wherein the processing and communication unit includes memory disposed to buffer transmissions of the input samples from the sensing and actuation unit to the deep learning module.

6. The device of any of 1-5, wherein the processing and communication unit includes memory disposed to buffer transmissions of the classification results from the deep learning module to the communication interface.

7. The device of any of 1-6, wherein the deep learning module is operative to receive the input samples from the sensing and actuating unit at a rate equal to or greater than an output rate of the sensing and actuating unit.

8. The device of any of 1-7, wherein the output rate of the sensing and actuating unit is a rate of conversion of analog signals from the one or the plurality of sensors into digital samples indicative of the physiological parameters.

9. The device of any of 1-8, wherein the deep learning module is operative to produce the classification results encoded with a number of bits within a total time that is equal to or less than a time requested by a medical or health application, wherein the total time is determined by a processing latency time to compute a single classification by the deep learning module multiplied by a number of classification cycles.

10. The device of any of 1-9, wherein the deep learning module is operative to produce the classification results at a rate that is less than a transmission rate of the communication interface and equal to or greater than a rate determined by a medical or health application.

11. The device of any of 1-10, wherein the neural network of the learning module comprises a convolutional neural network comprising a plurality of layers, each layer comprising one or more one-dimensional arrays.

12. The device of any of 1-11, wherein the plurality of layers of the neural network comprises an input layer, an output layer, and one or more hidden layers, and wherein each layer of the plurality of layers is configured with one or more of an activation function, weight, filter, or bias.

13. The device of any of 1-12, wherein the neural network comprises a convolutional neural network, an artificial neural network, a recurrent neural network, a feedforward network, a deep belief neural network, or a multi-layer perceptron.

14. The device of any of 1-13, wherein the plurality of layers includes one or more of a convolution layer, a dense layer, a fully-connected layer, a rectified linear layer, and a pooling layer.

15. The device of any of 1-14, wherein the neural network of the deep learning module is trained with data provided as a plurality of channels down-sampled to provide a plurality of one-dimensional arrays each representing samples from one of the plurality of channels.

16. The device of any of 1-15, wherein the input samples are provided as a plurality of channels, and the deep learning module is operative to:

predict classifications across space for each of the channels individually per a sampling time period, and/or to predict classifications across time intervals within each of the channels over a plurality of sampling time periods, and select a probable class output by a majority vote on a class output across one or both of the space or the time intervals.

17. The device of any of 1-16, wherein the deep learning module is trained with health application data, the health application data selected from the group consisting of electroencephalographic data, magnetoelectroencephalographic data, electrocardiographic data, electrooptical data, electromyographic data, blood pressure data, REM sleep duration data, glucose level data, data indicating a level in blood or tissue of a biomarker, biomolecule, pharmaceutical agent, or pharmaceutical formulation ingredient, data for a level of a dissolved gas or ion in blood, data for a level of pH, ionic strength or osmolality in blood.

18. The device of any of 1-17, wherein the deep learning module is trained with electroencephalographic data and is operative to classify the electroencephalographic data as one or more of a non-seizure state, a pre-seizure state, and a seizure state.

19. The device of any of 1-18, wherein the communication interface is operative to transfer data to an external device at an average data rate measured in bits per second that is equal to or greater than an average data rate of data determined by a medical or health application, and wherein the sensing and actuation unit is configured to carry out instructions based on the medical or health application.

20. The device of any of 1-19, wherein the communication interface includes a temporary memory storage operative to store bits produced by the learning module until a payload of one or more packets can be filled with the bits for transmission.

21. The device of any of 1-20, wherein the temporary memory storage has a minimum size of at least a number of bits per packet $B_{pkt}$ multiplied by a number of packets $K_{pkt}$.

22. The device of any of 1-21, wherein the temporary memory storage comprises a first in first out storage device.

23. The device of any of 1-22, wherein the communication interface has a data transmission rate $R_{tx}$ greater than an average rate $R_{DL}$ of bits produced by the learning module.

24. The device of any of 1-23, wherein the communication interface is operative to transmit the classification results from the learning module to an external device and to receive actuation instructions from the external device.

25. The device of any of 1-24, further comprising a wireless ultrasonic communication interface to an external device.

26. The device of any of 1-25, wherein the sensing and actuation unit comprises one or a plurality of analog sensors of one or more physiological parameters and an analog to digital converter operative to convert analog signals from the at least one analog sensor indicative of the one or more physiological parameters into digital samples for transmission to the processing and communication unit.

27. The device of any of 1-26, wherein the sensing and actuation unit is operative to convert the analog signals into the digital samples at a conversion rate $R_{conv}$ determined by a number $N_s$ of the analog sensors, an average number of voltage values $\bar{r}_{sens}$ transmitted by the one or the plurality of analog sensors, a conversion resolution $\eta$ of the analog to digital converter, and a latency $t_{conv}$ of the analog to digital converter for a single sample.

28. The device of any of 1-27, further comprising a temporary storage buffer in communication with the sensing and actuating unit to temporarily store the input samples received from the sensing and actuating unit, the temporary storage buffer comprising storage for at least a minimum number of bits that can be processed by the deep learning module before the sensing and actuating unit terminates conversion of the analog signals into the digital samples.

29. The device of any of 1-28, wherein the processing and communication unit is further operative to determine, based on the classification results from the learning module, instructions for the sensing and actuation unit and to transmit the instructions to the sensing and actuation unit.

30. The device of any of 1-29, wherein the processing and communication unit is operative to reconfigure the neural network to change one or more of the physiological parameters that are classified.

31. The device of any of 1-30, further comprising a power unit disposed to provide power to the processing and communication unit and the sensing and actuation unit.

32. The device of any of 1-31, wherein the sensing and actuation unit and the processing and communication unit are disposed within a single implantable housing.

33. The device of any of 1-32, wherein the one or more implantable sensors are selected from the group consisting of a motion sensor, a gyroscope, an accelerometer, a cardiac rhythm monitor, a heart rate monitor, a pulse monitor, a blood pressure sensor, a glucose sensor, a drug pump monitor, a sleep sensor, a REM sleep duration sensor, a still camera, a video camera, a sensor for one or more biomolecules, a sensor for one or more pharmaceutical agents or pharmaceutical formulation ingredients, a sensor for a dissolved gas or ion, and a sensor for pH, ionic strength or osmolality.

34. The device of any of 1-33, wherein the one or more actuators are selected from the group consisting of a drug pump, a heart stimulator, a heart pacemaker, a bone growth stimulator, a deep brain stimulator, a neurostimulator, and a neuromuscular electrical stimulator.

35. A method of sensing and classifying physiological parameters of a body, comprising:
(a) implanting the device of any of 1-34 into the body;
(b) transmitting input samples from the sensing and actuating unit to the communication and processing unit;
(c) classifying the input samples into classification results; and
(d) one or both of:
at the communication interface, transmitting the classification results to an external device, and
at the processing and communication unit, determining instructions, based on the classification results, for the sensing and actuation unit and transmitting the instructions to the sensing and actuation unit.

36. The method of 35, wherein the body is a human body or a non-human animal body.

37. The method of any of 35-36, wherein the classification results include one or more of a non-seizure state, a pre-seizure state, and a seizure state.

38. A method of embedding deep learning into an implantable medical device, comprising:
(a) training a deep learning module including a neural network having a plurality of layers with a set of physiological data; and
(b) providing an implantable medical device comprising:
a sensing and actuation unit comprising one or more implantable sensors operative to sense physiological parameters of a body and one or more actuators; and
a processing and communication unit, in communication with the sensing and actuation unit, comprising:
the deep learning module trained in step (a) and operative to receive input samples from the sensing and actuation unit, the deep learning module including a neural network trained to process the input samples through a plurality of layers to classify the physiological parameters sensed by the sensing and actuation unit and provide classification results, and
a communication interface in communication with the deep learning module to receive the classification results, the communication interface comprising an ultrasonic transceiver to transmit and receive ultrasonic signals through biological tissue.

39. The method of 38, wherein processing and communication unit comprises one or more logic devices, and the deep learning module is implemented in circuitry of the one or more logic devices.

40. The method of any of 38-39, wherein the deep learning module is trained on a computer external to the implantable medical device and converted for implementation in the circuitry after training.

41. The method of any of 38-40, further comprising providing the implantable medical device with memory disposed to buffer transmissions of the input samples from the sensing and actuation unit to the deep learning module.

42. The method of any of 38-41, further comprising forming the deep learning module to produce classification results encoded with a number of bits within a total time that is equal to or less than a time requested by a medical or health application, wherein the total time is determined by a processing latency time to compute a single classification by the deep learning module multiplied by a number of classification cycles.

43. The method of any of 38-42, further comprising forming the deep learning module to produce classification results at a rate that is less than a transmission rate of the communication interface and equal to or greater than a rate determined by a medical or health application.
44. The method of any of 38-43, wherein the neural network of the deep learning module is formed as a convolutional neural network and each layer of the plurality of layers comprises one or more one-dimensional arrays.
45. The method of 38-44, further comprising forming the communication interface to transfer data to an external device at an average data rate measured in bits per second that is equal to or greater than an average data rate of data determined by a medical or health application, and wherein the sensing and actuation unit is configured to carry out instructions based on the medical or health application.
46. The method of any of 38-45, further comprising forming the communication interface with temporary storage memory operative to store bits produced by the learning module until a payload of one or more packets can be filled with the bits for transmission.
47. The method of any of 38-46, wherein the temporary storage memory has a minimum size of at least a number of bits per packet $B_{pkt}$ multiplied by a number of packets $K_{pkt}$.
48. The method of any of 38-47, wherein the temporary storage memory comprises a first in first out storage device.
49. The method of any of any of 38-48, wherein the communication interface has a data transmission rate $R_{tx}$ greater than an average rate $R_{DL}$ of bits produced by the learning module.
50. The method of any of 38-49, further comprising forming the sensing and actuation unit to convert analog signals into digital samples at a conversion rate $R_{conv}$ determined by a number $N_s$ of the one or more implantable sensors, an average number of voltage values $\bar{r}_{sens}$ transmitted by the one or more implantable sensors, a conversion resolution $\eta$ of an analog to digital converter, and a latency $t_{conv}$ of the analog to digital converter for a single sample.
51. The method of any of 38-50, wherein the deep learning module is trained with health application data, the health application data selected from the group consisting of electroencephalographic data, magneto-electroencephalographic data, electrocardiographic data, electrooptical data, electromyographic data, blood pressure data, REM sleep duration data, glucose level data, data indicating a level in blood or tissue of a biomarker, biomolecule, pharmaceutical agent, or pharmaceutical formulation ingredient, data for a level of a dissolved gas or ion in blood, data for a level of pH, ionic strength or osmolality in blood.
52. The method of any of 38-51, wherein the deep learning module is trained with electroencephalographic data and is operative to classify the electroencephalographic data as one or more of a non-seizure state, a pre-seizure state, and a seizure state.
53. The method of any of 38-52, wherein the deep learning module is trained with data comprising a plurality of channels down-sampled to provide a plurality of one-dimensional arrays each representing samples from one of the plurality of channels.

DETAILED DESCRIPTION

Figure 1:
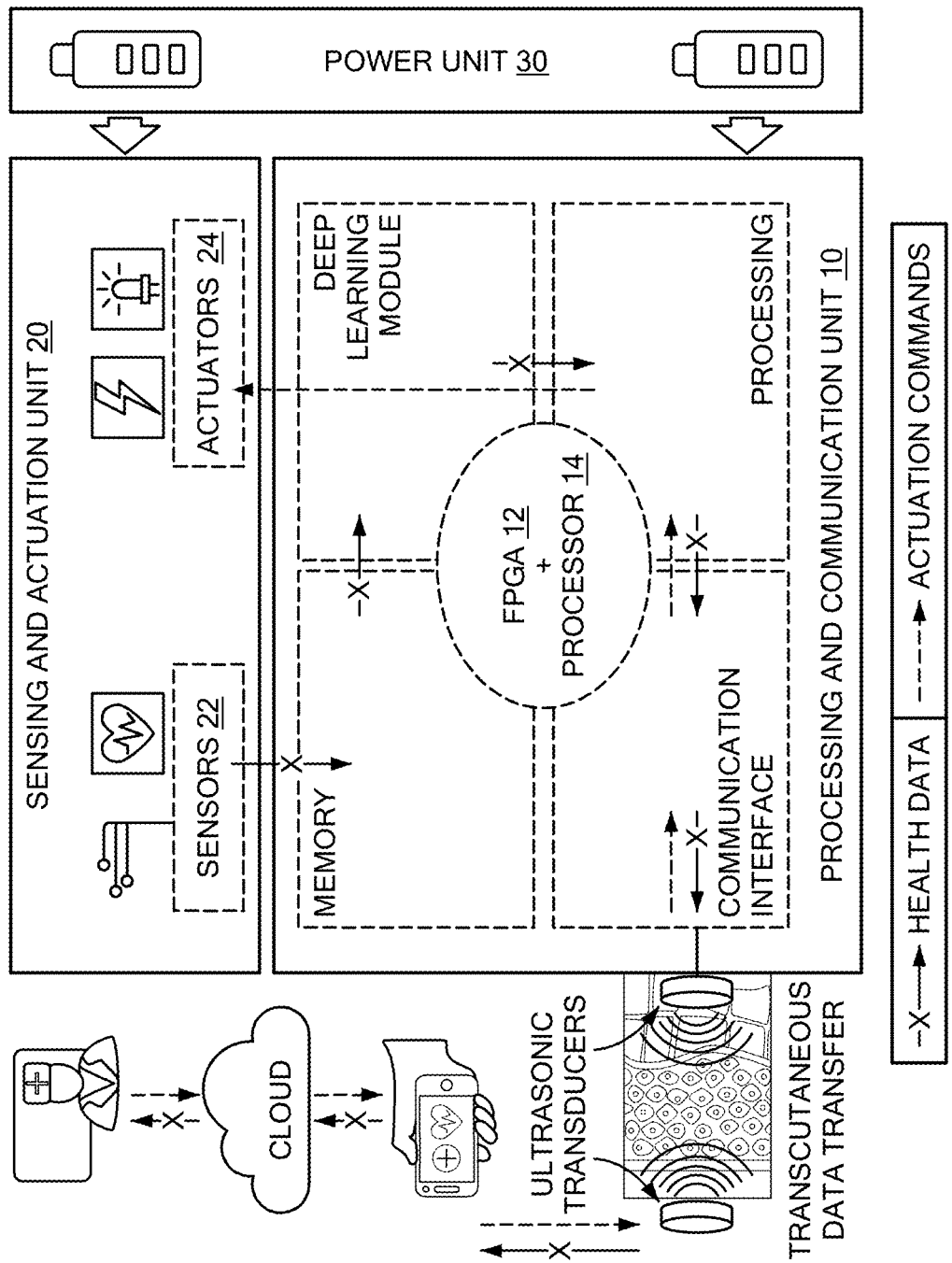
FIG. 1 is a schematic illustration of an embodiment of an embedded networked deep learning system.

Deep learning (DL) uses computational models composed of multiple layers to learn representations of large data sets and perform classification tasks directly from its inputs. Although recent research in implantable medical devices has made steps toward the Internet of Implantable Medical Things (IoIMT), it is still unknown (i) whether DL techniques can be successfully integrated inside a resource-challenged embedded implantable system; and (ii) whether hardware-based DL can provide better energy and latency performance with respect to a CPU-based or cloud-based offloading of the learning task. The amount of data and parameters of a deep neural network can be daunting for resource-constrained embedded IoIMT systems.

The present technology provides an embedded networked deep learning (ENDL) platform, which fills a gap between cloud-based deep neural network systems and the harsh environment of the human body. In some embodiments, the technology provides a deep learning medical device implantable in a body that can include (i) a hardware-based convolutional neural network (CNN) that interfaces with a series of implantable sensors; and (ii) a wireless ultrasonic interface that sends the classification results to an external device and/or receives actuation commands. To study the necessary trade-offs between latency and resource consumption, a mathematical model is also provided of the interactions between the components of the device.

The device has been prototyped on a system-on-chip platform and its end-to-end capabilities are demonstrated on an application to predict seizures in epileptic patients, where the models are trained using real intracranial electroencephalogram (iEEG) data. Extensive experimental results on porcine meat as transmission medium shows that (i) the embedded CNN has an accuracy as high as 100% with boosting—which is comparable to cloud-based DL performance; (ii) the ENDL platform with FPGA-based CNN runs with 9× less latency than a CPU-based CNN approach, and consumes 4.5× less energy than a cloud-based approach—leading to a 10× battery lifetime improvement.

The technology can provide features including a working convolutional neural network (CNN) for seizure prediction on a field programmable gate array (FPGA); an ultrasonic transducer with physical layer for ultrasonic communication; performance of classification vote to boost prediction accuracy; and achieve an accuracy between 80 and 100% depending on patient dataset and boosting scheme.

The technology can include a boosting scheme than can improve the validity of neural network predictions, improved latency by nine times as compared to full CPU base system; four and a half times less energy consumption than a cloud-based neural network, and capabilities to communicate predictions with the outside world.

The technology is useful for a variety of applications, including without limitation, predicting onset of epileptic seizures well before occurrence; performing actuation to mitigate effects of seizures; notifying healthcare personnel on patient condition(s); and predicting other negative health events from different sensor inputs.

The technology can be used for treating epilepsy by predicting seizure onset and offering communication of prediction results for health monitoring and potential treatment actuation.

The technology can be used for activating treatment after prediction of seizure. The technology is not limited to seizures. The technology provides a predictor that can be trained on different sensor data of body stimuli, including other brain and cardiac activities, among others.

The technology is useful, because patients can be remotely monitored, reducing healthcare costs. Also, the use of edge computing does not require cloud servers which are costly. Also the technology can result in decreased energy consumption and increased device lifetime. The technology is useful because edge computation and FPGA implementation allow for less latency and energy consumption meaning faster predictions and longer device lifetime. The technology can include the addition of ultrasound transmission, which can allow for Internet of Things integration.

I. Introduction

The deluge of implantable medical devices (IMDs) already on the consumer market is bringing a revolution to the healthcare business. About 32 million Americans (one in ten) already benefit from medical implants, including pacemakers, defibrillators, neuro-stimulators, artificial joints, stents, and heart valves. The increasing age of the world population will increase the desirability and usefulness of implantable medical devices. Sensor technology is also improving. Modern-era implantable sensors, capable of interfacing directly with internal organs and collecting large volumes of clinical quality data each second, can enable real-time sensing capabilities.

The technology described herein can enable the integration of in-situ deep learning (DL) algorithms for early detection of diseases with modern sensor technology and IMDs. DL algorithms are in many cases substantially better in terms of medical event detection than experienced physicians. For example, in some instances, deep learning-based networks can classify epileptic signals with an accuracy greater than 95%. In another example, DL has been shown to outperform known machine learning algorithms in terms of classification rate of movement disorders such as Parkinson's disease. Another advantage of DL algorithms as used herein is that they are application-insensitive, meaning that the same CNN architecture can be tailored to different patients by changing the model's parameters. Thus, if the CNN is implemented in hardware, this can allow the same circuits to be reused for multiple patients. Described further in Section III below is an example of how a CNN can be reused to control different patients' EEGs.

The Need for Embedded Networked Deep Learning

A limitation of known DL-based medical inference is that current prior art analysis, classification and processing of DL-based critical physiological signals does not happen in real-time but it is instead executed offline in the cloud, where machines have resources that are far beyond what a tiny IMD can offer. For example, proposed DL algorithms for healthcare applications have shown high levels of accuracy (>90%) but require a 2.50 GHz CPU with 16 GB of RAM, which cannot be implemented on an IMD where CPUs have a handful of megahertz and memories have a handful of kilobytes.

Cloud-based offloading is certainly an option. However, as shown in Section IV, the transfer process of sensor data from the IMD to the cloud necessarily impacts on the latency (4× in the experiments described herein)—an issue in health-critical applications where the response time becomes critical. Moreover, besides the computational and networking aspects, cloud-based systems almost completely neglect the energy efficiency aspect—which is a consideration in IMD technology. This is because IMDs often require non-trivial surgery for battery replacement. Thus, increasing the battery lifetime by reducing the energy consumption can be a significant issue in IMDs.

The technology described herein can integrate the numerous advances on miniaturization, sensing, and communications of IMDs with an embedded knowledge inference domain. The present technology can accordingly take advantage of the full potential of the Internet of Implantable Medical Things by enabling learning and wireless networking capabilities to reside together on the same embedded system. To this end, the technology described herein provides embodiments of an embedded networked deep learning (ENDL), a platform that can bridge the gap between the current IMDs and DL-based medical inference.

As illustrated in FIG. 1, is some embodiments, the technology provides a deep learning medical device that includes a processing and communication unit 10 built on one or more logic devices 12, such as a field-programmable gate array (FPGA). A processing unit (CPU) 14, which can be either soft core (i.e., implemented in the FPGA) or hard core (i.e., on its own integrated circuit), can provide additional computational resources. A sensing and actuation unit 20 includes one or more implantable sensors 22 and one or more actuators 24. A power unit 30 is provided to power the other two units. The components can be enclosed within a single implantable housing.

Due the severe path loss introduced by the human tissue, the device technology can refrain from using RF-based communications and can use ultrasound-based communication to increase the overall data rate. In some embodiments, the DL classification results can be processed on board for immediate action, realizing an on-board sensing-processing/actuation closed-loop. Alternatively or additionally, in some embodiments, the DL classification results can be sent to a receiving device (external to the body) through an ultrasonic communication interface. In this manner, decisions on the specific actuation to perform can also be sent to the device from outside.

The device can bring to the 1 MB landscape an implementation of hardware-based embedded deep learning. Additionally, the IMDs can be used to address critical health issues such as real-time in situ seizure prediction. The IMD-located DL of the technology is more energy-efficient and presents less latency than cloud-based offloading. The technology described herein provides a system model derived to aid with the design and a mathematical formulation derived to account for all the process latencies, memory requirements and transfer data rates between its components (described further in Section II). The technology provides a neural network, such as a convolutional neural network (CNN) designed, trained, and tested for early seizure prediction from human intracranial EEG data sets (described further in Section III). The accuracy of the hardware-based CNN is shown in some embodiments to be between 66% and 100% with boosting (described further below), which is comparable to cloud-based DL performance.

A prototype of the device has been implemented on a system-on-chip device and compared through a porcine meat testbed with a cloud-based offloading system and a system where learning is done on the CPU (described further in Section IV). Results show that the device with hardware-based CNN ran with 9× less latency than a CPU-based CNN approach, and consumed 4.5× less energy than a cloud-based approach—leading to a 10× improvement in battery lifetime.

II. Design and Constraints

Figure 2:
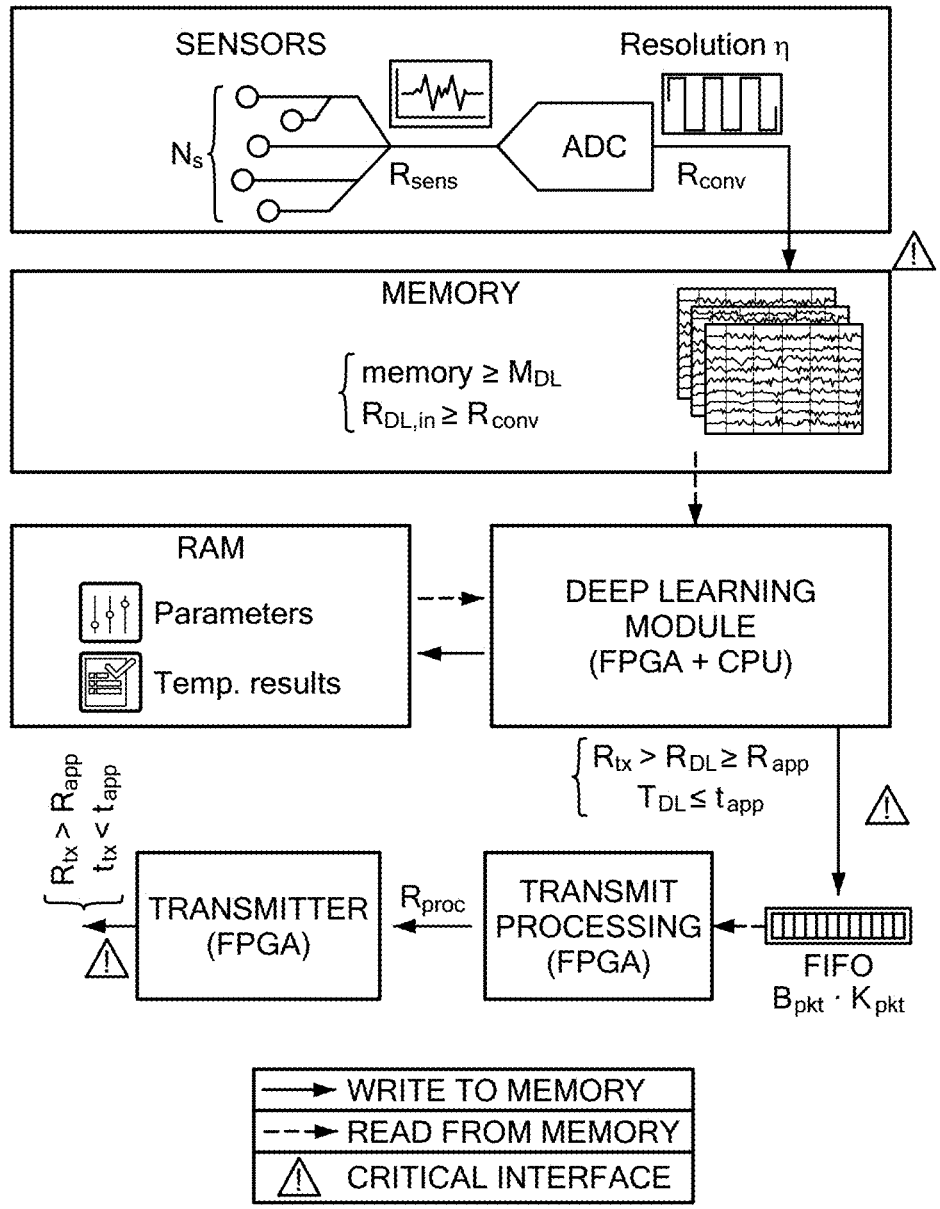
FIG. 2 is a schematic illustration of an embedded networked deep learning system showing interaction of components with each other and between components and buffers. Certain interfaces that play a role in the design of the system are indicated with an exclamation point symbol.

FIG. 2 illustrates a block diagram of an embodiment of an embedded deep learning device where certain interfaces, addressed from a design point of view, have been marked with an exclamation point symbol. The design of an implantable device that performs sensing/actuation operations and communicates with an external unit is determined by multiple constraints, including the amount of data produced by the sensor(s) and an analog-to-digital converter (ADC) of the sensing and actuating unit, and the minimum required data rates. Therefore, a model of the system is provided that allows the design of suitable interfaces for transferring data between its internal components and to external devices. Two requirements that are addressed are the minimum data rate to be implemented at the communication interface and the amount of data to be processed in a time unit, as these requirements affect (i) the minimum processing time of the DL module, and (ii) the minimum memory size. Memories are provided at two interfaces: (a) the interface between the sensor unit and the processing unit, and (b) the interface between the processing unit and the communication unit.

The implementation of the ENDL system connects expertise from extremely different domains—deep learning and embedded system design. Some design constraints and challenges on the system design side include providing enough memory buffers to interface components that operate and generate information bits with different timings while at the same time saving memory resources. Thus, part of the efforts include (i) decreasing the RAM and computational resources required during the implementation phase of the CNN on hardware; and (ii) reducing the execution latency of the DL algorithm to ensure that the real-time condition posed by the specific health application is respected. For this reason, a system model of the interactions is provided between components and a mathematical formulation is provided to systematically account for the latency of each process, the amount of bits exchanged between components and the transfer data rates at adjacent interfaces.

Challenges addressed on the learning side include: (i) defining an optimal deep neural network structure; and (ii) finding a trade-off between the depth of the network, the number of parameters, and the size of the input while still obtaining a classification accuracy comparable to cloud-based approaches (e.g., in some applications, greater than 80%). In Section III, it is demonstrated with respect to a complex intracranial electroencephalogram (iEEG) signal recording that: (i) a CNN can be embedded in hardware on an FPGA; (ii) it can realize early seizure prediction to treat a serious issue such as epilepsy; and (iii) the result accuracy is comparable with state-of-the art DL algorithms.

A. Timings Constraints

Each specific medical application requires a certain type or types of information to be gathered inside of the body and transferred to an external device, or to the cloud, at periodic intervals or at a certain bitrate. This requirement translates to strict constraints that must be met at the communication interface. Suppose that the health information is encoded into $B_{app}$ bits that are requested each $t_{app}$ seconds, which leads to the minimum required average bit rate of the application $R_{app}=B_{app}/t_{app}$ (in bit/s).

Condition I. The communication unit introduces a short computational delay to process the bits before they are transmitted. Let $t_{proc}$ be the processing time for each bit and $R_{proc}=1/t_{proc}$ be the amount of bits processed in a time unit inside the transmission module before transmission. Call $t_{tx}=1/R_{tx}$ the 1-bit transmit time in [s], where $R_{tx}$ in bit/s is the transmission rate. The transmitter has to be able to transfer at an average rate Rix equal or larger than $R_{app}$.

Condition I only defines the data rate requirement of the communication unit, but it is not sufficient to guarantee that the system can produce enough information bits to meet the requirements. Toward this end, another condition on the DL module has to be defined.

Condition II. The DL module introduces a processing latency $t_{DL}$, to compute a single classification. The result of the classification is encoded with $B_{DL}$ bits. Thus, the DL module produces (and transfers to the communication unit) information bits at an average rate of $R_{DL}=B_{DL}/t_{DL}$ bit/s. If it is assumed that the application requires a number of $B_{app}$ bits equal or larger than $B_{DL}$ per time unit, then the DL module has to execute $N_c=\lceil B_{app}/B_{DL}\rceil$ classification cycles to generate $B_{app}$ bits. These operations require a total time ($T_{DL}$, highlighted in FIG. 3) equal to the product between the number of executions of the DL algorithm and the DL processing latency, i.e., $T_{DL}=N_c \cdot t_{DL}$.

In any case, the $B_{app}$ bits must be generated by the DL module in time to be ready for transmission at most in an interval equal to $t_{app}$, meaning before the starting point of the next $t_{proc}$ interval. The timing diagram is reported in FIG. 3.

To avoid memory overflows $R_{DL}$ has to be smaller only than $R_{tx}$; since, in general, $R_{proc} > R_{tx}$, the processing latency $t_{proc}$ of the transmission module does not affect the choice of $R_{DL}$. At the same time, the DL module has to respect another minimum limit and produce at least $B_{app}$ bits in the interval $T_{DL}$, such that $T_{DL} \leq t_{app}$. Hence, the condition on the output data rate is given by:

$$R_{tx} > R_{DL} = \frac{B_{DL}}{t_{DL}} = \frac{B_{app}}{T_{DL}} \geq R_{app}. \quad (1)$$

Figure 3:
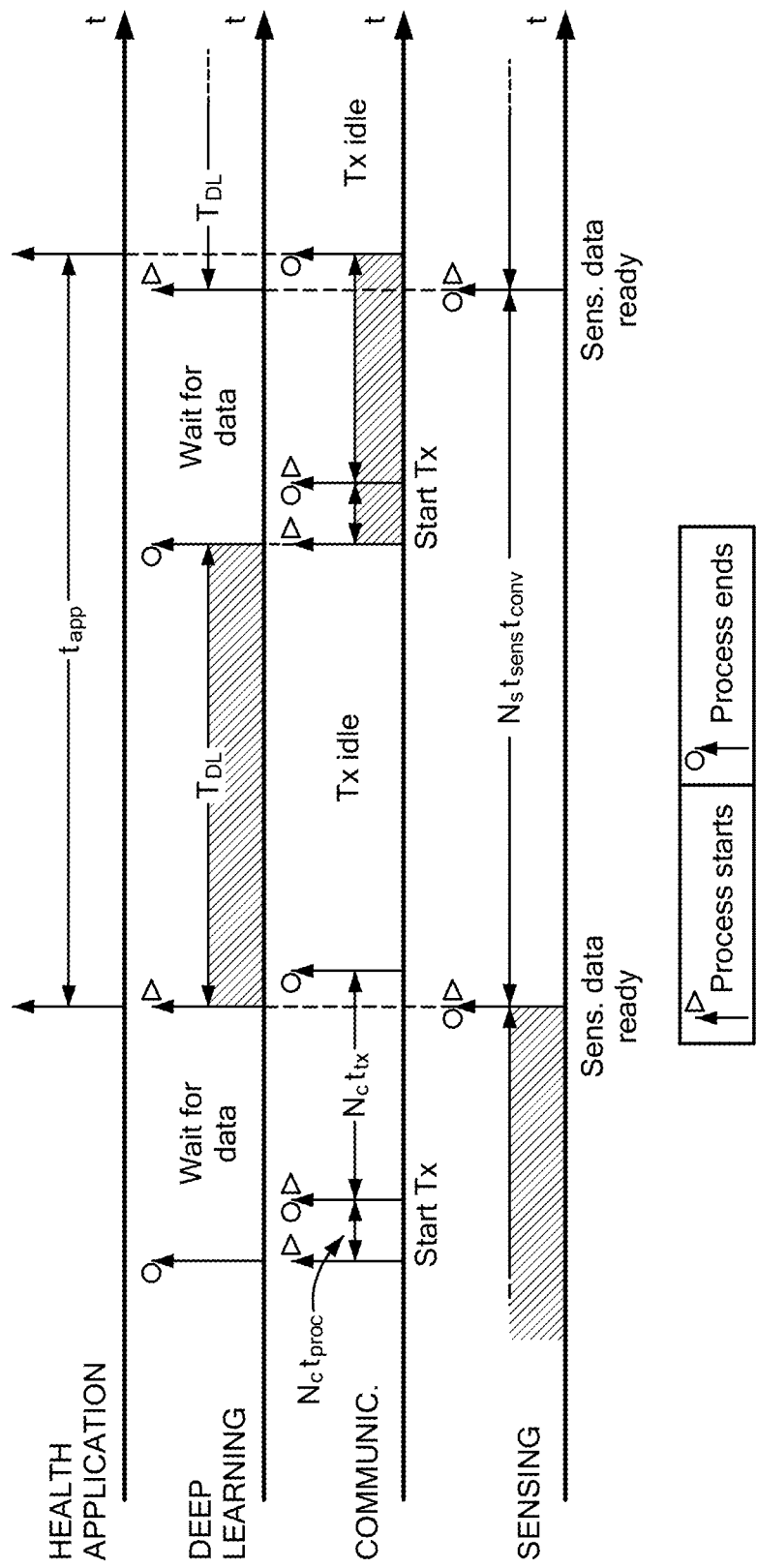
FIG. 3 illustrates a timing diagram for a health application. An acquisition-conversion-deep learning-transmission end-to-end task is shaded. The sensing-and-conversion process starts in the previous task.

Condition II ($T_{DL} \leq t_{app}$) and equation (1) can be visualized in FIG. 3.

This analysis assumes that the deep learning module and the communication interface operate in parallel, so that the DL module can start a new classification execution while the transmitter is still processing/sending the previous results. If such parallelization is not possible, then $T_{DL} \leq t_{app} - N_c \cdot (t_{proc} + t_{tx})$.

B. Memory Constraints

The data exchange between the sensing and actuating unit and the processing and communication unit requires a memory to temporarily store the sensed data. The design of such memory depends on two factors: (i) the conversion rate of the ADC (number of bits generated per second), and (ii) the number of input samples that the DL algorithm reads from the memory at the beginning of each classification cycle. The sensing unit includes one or several analog sensors followed by an ADC. In a more general case, the sensors can be heterogeneous and collect different biomarkers, each with a specific response time $t_{sens}^{(i)}$, where $i \subseteq [1,N_s]$ and $N_s$ is the number of sensors.

$$r_{sens}^{(i)} = 1/t_{sens}^{(i)}$$

is the number of voltage values that each sensor i forwards to the ADC per unit of time. The cumulative rate of voltage values per unit of time of the $N_s$ sensors before digitization is $$R_{sens} = \sum_{i=1}^{N_s} r_{sens}^{(i)}.$$

If the sensors are all of the same type, $R_{sens}$ is $N_s \cdot \bar{r}_{sens}$, where $$r_{sens}^{(i)} = \bar{r}_{sens}, \forall i \subseteq [1, N_s].$$

The ADC converts the analog input signals into digital samples with a resolution of η bits per sample. The cumulative conversion rate ($R_{conv}$ in bit/s) of the ADC, for homogeneous sensors, is $$R_{conv} = (N_s \cdot \bar{r}_{sens}) \cdot \eta \cdot \frac{1}{t_{conv}}, \quad (2)$$

where $t_{conv}$ is the ADC conversion latency for a single sample.

Condition III. The DL module executes the classification algorithm every $T_{DL}$ seconds, at most. The DL algorithm takes in input $M_{DL}$ bits and must process them before the sensing unit terminates its conversion. Thus, the minimum required buffer between the sensing unit and the DL module is of $M_{DL}$ bits while, at the same time, the number of bits that the DL module can read per second ($R_{DL,in} = M_{DL}/T_{DL}$) has to be equal or larger than the output rate of the ADC:

$$R_{DL,in} > R_{conv}. \quad (3)$$

Condition IV. The transmitter module in the communication interface transfers data in packets of $B_{pkt}$ bits. The packets can be transmitted one at the time or in bursts of $K_{pkt}$. A FIFO is needed at the interface between the two modules to momentarily store the bits produced by the DL module before enough bits are produced to fill the payload(s) of one or more packets. Based on the fact that the transmitter transfers the data in bursts of packets, the minimum size of the FIFO can be set to $B_{pkt} \cdot K_{pkt}$ bits. Condition II ($R_{tx} > R_{DL}$) assures that if the FIFO is long enough there is no overflow.

III. Use-Case: Seizure Prediction

To demonstrate the capabilities of the embedded deep learning technology described herein, the problem of DL-based seizure prediction is discussed. Seizures are a unique, rapid, and rhythmic firing of neurons that cause different symptoms depending on location in the brain.

A. Problem Definition

The states of epilepsy fall into three categories: non-seizure (interictal), pre-seizure (preictal), and seizure (ictal). Classifying the pre-seizure state is key to seizure prediction. This is generally challenging as the difference between the two states, pre-seizure and seizure, is not easily visualized and it can be approximated by linear or non-linear methods. The device disclosed herein is described in relation to CNN-based seizure prediction; however, the device can be readily employed and/or adapted for pre-seizure detection as appropriate, depending on the application.

Figure 4:
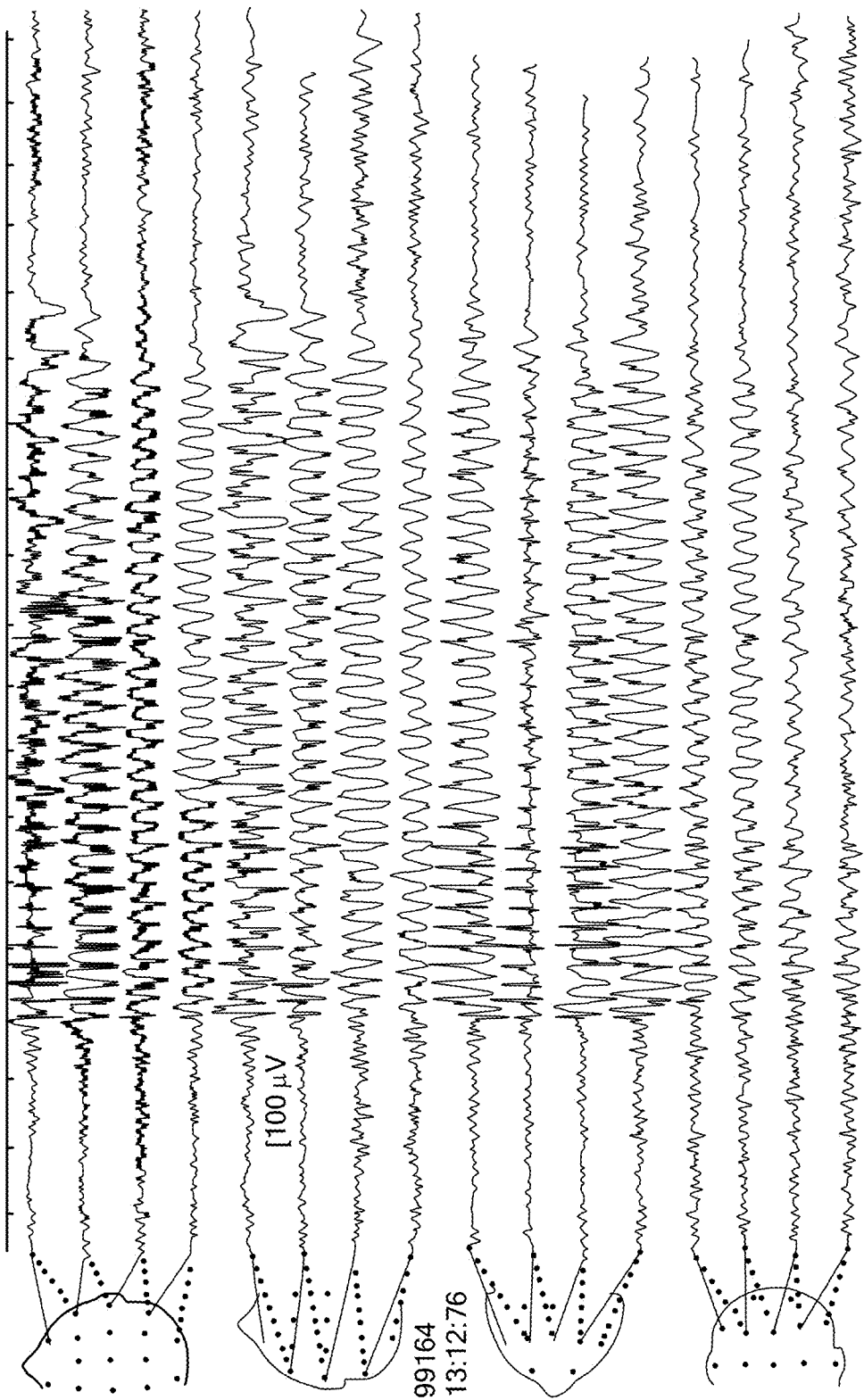
FIG. 4 illustrates a 16-channel EEG of a generalized seizure.

Seizures themselves fall into two main categories, general and partial (focal). General seizures occur throughout most of the brain, while partial seizures are localized to a specific area of the brain. This is important when considering the way that seizures are measured which is with an electroencephalogram (EEG) or intracranial electroencephalogram (iEEG). The EEG, or iEEG, is a method to measure electrical activity in multiple channels by the use of several electrodes placed either on or in the head, respectively. Each channel of an EEG or iEEG measures the electrical change between a pair of electrodes at a different location. Depending on the type of seizure (general or partial) and placement of the electrodes, some channels will not experience the drastic changes that other channels detect, as seen in FIG. 4. This can be taken into account when deciding how to feed data to the CNN as discussed more in Section III-B.

B. Training and Testing Data

Training can be described in conjunction with an iEEG data set obtained from the American Epilepsy Society. The data set includes data from two human patients, both sampled at 5 kHz and broken into 10 minute samples over the span of hours with both pre-seizure and non-seizure data. The first patient's iEEG contains 15 channels while the second patient's contains 24 channels. The pre-seizure samples are defined as iEEG data measured from 65 to 5 minutes before a seizure; data registered before 65 minutes are non-seizure samples. This means that 5 minutes before the seizure the CNN should have already predicted the seizure, and notified the system to begin actuation or notification. The dataset is split as: 80% for training, 10% for validation, and 10% for testing.

Figure 5:
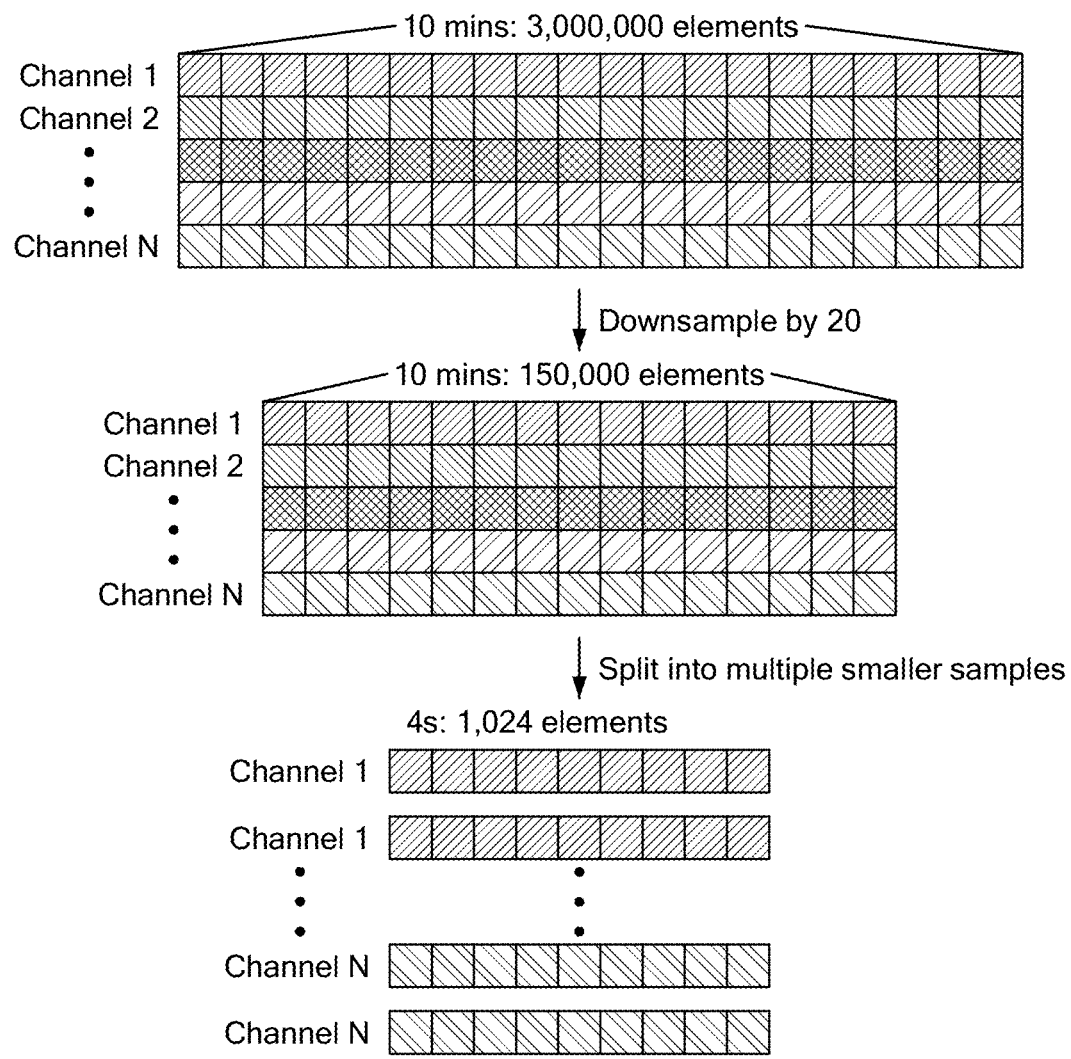
FIG. 5 illustrates an example of CNN data preprocessing.

First, the data is down-sampled by a factor of 20 to bring the sampling frequency from 5 kHz to 250 Hz. Then, the channels of the 10 minute sample are separated into their own samples and broken into smaller 4 second samples. This is done to decrease the amount of block random access memory (BRAM) used in the FPGA, as the BRAM is used to store the input and parameters of the CNN. The pre-processing is illustrated in FIG. 5. The input to the CNN is a 1-dimensional array of size 1024 elements (each represented by 32 bits), representing a 4 second sample from only one iEEG channel. Only one channel is chosen due to the varying presence that a seizure can have on different channels of an iEEG. This also allows for the model to be easily adaptable to iEEGs of varying number of channels. This model, therefore, only predicts seizures on a per-channel basis. A majority vote algorithm among all the channels in a given sample interval can be used to boost accuracy as discussed further in Section III-D.

C. CNN Model Architecture and Training

Figure 6:
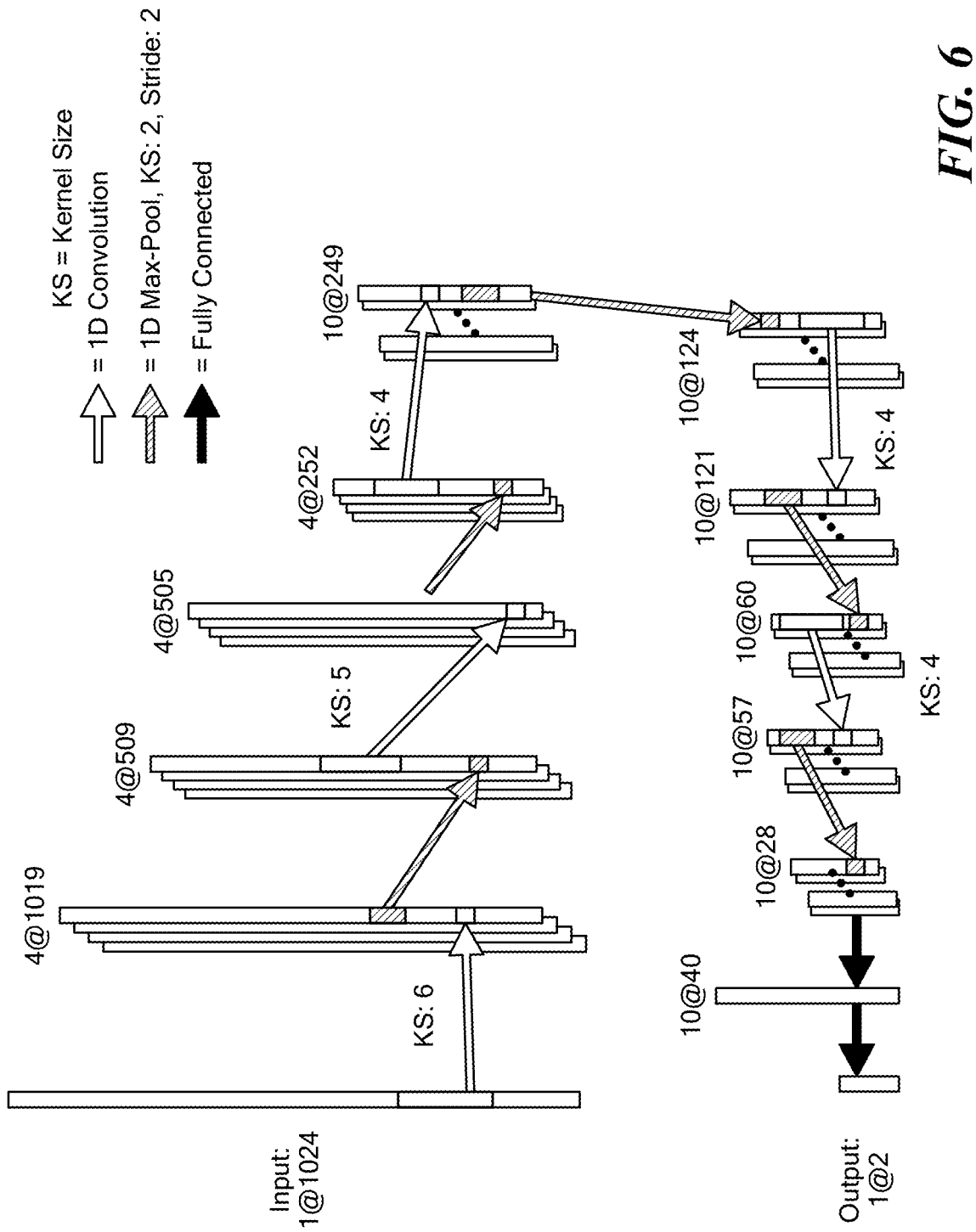
FIG. 6 illustrates an embodiment of a deep learning neural network employing a 12-layer 1-dimensional CNN to classify pre-seizure and non-seizure iEEG samples.

In some embodiments, a suitable CNN can be 1-dimensional with 12 layers as shown in FIG. 6. A suitable CNN can be based on a CNN such as that is described in Acharya et al. (U. R. Acharya, S. L. Oh, Y. Hagiwara, J. H. Tan, and H. Adeli, "Deep convolutional neural network for the automated detection and diagnosis of seizure using EEG signals," *Computers in biology and medicine*, vol. 100, pp. 270-278, 2018.) The main difference is the number of parameters, which are down to 12,424. This specific architecture gives suitable results. Every convolutional layer uses a LeakyReLU activation, while the last layer uses a Softmax activation function. Max-pooling layers utilize stride of 2. The network only has two output classes, pre-seizure and non-seizure, without actually classifying the seizure itself. This is because iEEG readings of a seizure itself contain higher energy spikes then both pre-seizure and non-seizure readings, which are fairly indistinguishable. Therefore, calculating the energy of the iEEG readings periodically may be enough to detect the seizure as it is happening. In some embodiments, the network can be built utilizing Python with the Keras API on top of a TensorFlow back-end. The CNN can be trained with a learning rate of 0.0001 in batches of 100 with the Adam optimizer. However, it will be appreciated that the particular neural network and training can be selected depending on the application.

D. Seizure Prediction Boosting

Figure 7:
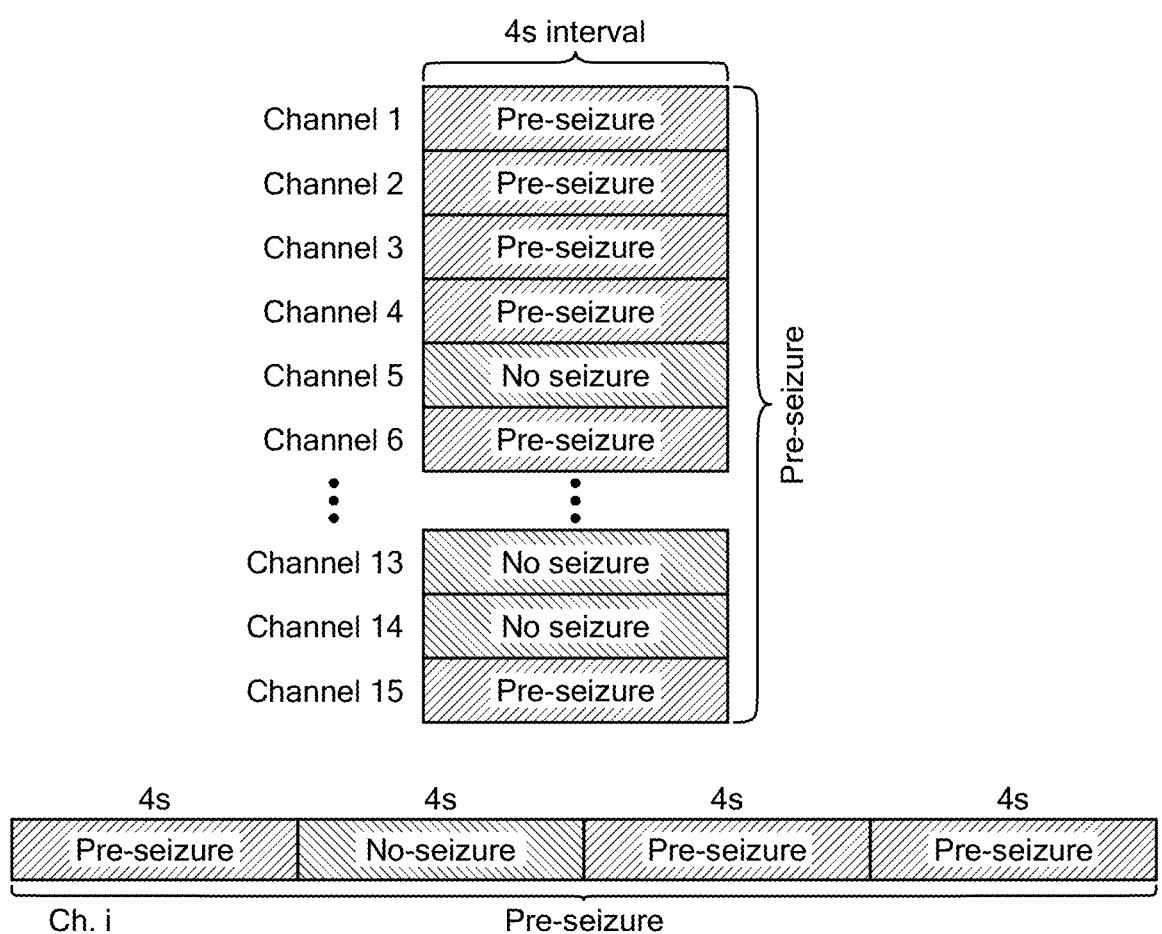
FIG. 7 illustrates examples of CNN seizure prediction. The top figure illustrates CNN predictions of a 15 channel iEEG in a 4-second sampling period. The bottom figure illustrates CNN predictions of a single channel over 12 seconds.

All the channel predictions in a sample interval can be used to boost the classification accuracy by way of majority vote without increasing memory consumption. This concept is illustrated in FIG. 7 (top), which shows a 15 channel iEEG in a 4 second sample interval with all the CNN predictions for each channel.

With generalized seizures, which are visible among most of the channels, voting across channels can be beneficial. But for a partial seizure which may not show up on every channel this can hurt the classification. To this end, a majority vote can be taken across time as well as space, as shown on the bottom portion of FIG. 7. By combining the two methods, it can also be known how many individual channels are experiencing a seizure and whether or not it is generalized or partial. For the channel vote case, as illustrated on the top portion of FIG. 7, the number of successful classifications, within a sample interval, can be modeled as a binomial random variable $X \sim B(n_c, p)$, where $n_c$ is the total number of channels in the iEEG, and $p$ is the probability of success or the accuracy of the CNN for a single channel. The probability mass function (PMF) of $X$ calculates the probability that k out of $n_c$ iEEG channels are classified correctly and the cumulative distribution function (CDF) calculates the probability that there are less than or equal to k correct classifications out of $n_c$. From the CDF, the probability of a correct final decision for a time interval by taking a majority vote can be calculated. This, by definition of majority vote, is the probability that the number of successes are in the majority, or at least greater than half of the iEEG channels within the time interval. This is expressed by:

$$P\left(X > \left\lfloor \frac{n_c}{2} \right\rfloor\right) = 1 - F_X\left(\left\lfloor \frac{n_c}{2} \right\rfloor\right) \qquad (4)$$

$$= 1 - \sum_{h=0}^{\lfloor n_c/2 \rfloor} \binom{n_c}{h} p^h (1-p)^{n_c-h}$$

$$= \sum_{h=\lfloor n_c/2 \rfloor}^{n_c} \binom{n_c}{h} p^h (1-p)^{n_c-h}$$

where $$\left\lceil \frac{n_c}{2} \right\rceil$$

is the ceiling of $$\frac{n_c}{2}.$$

Figure 8:
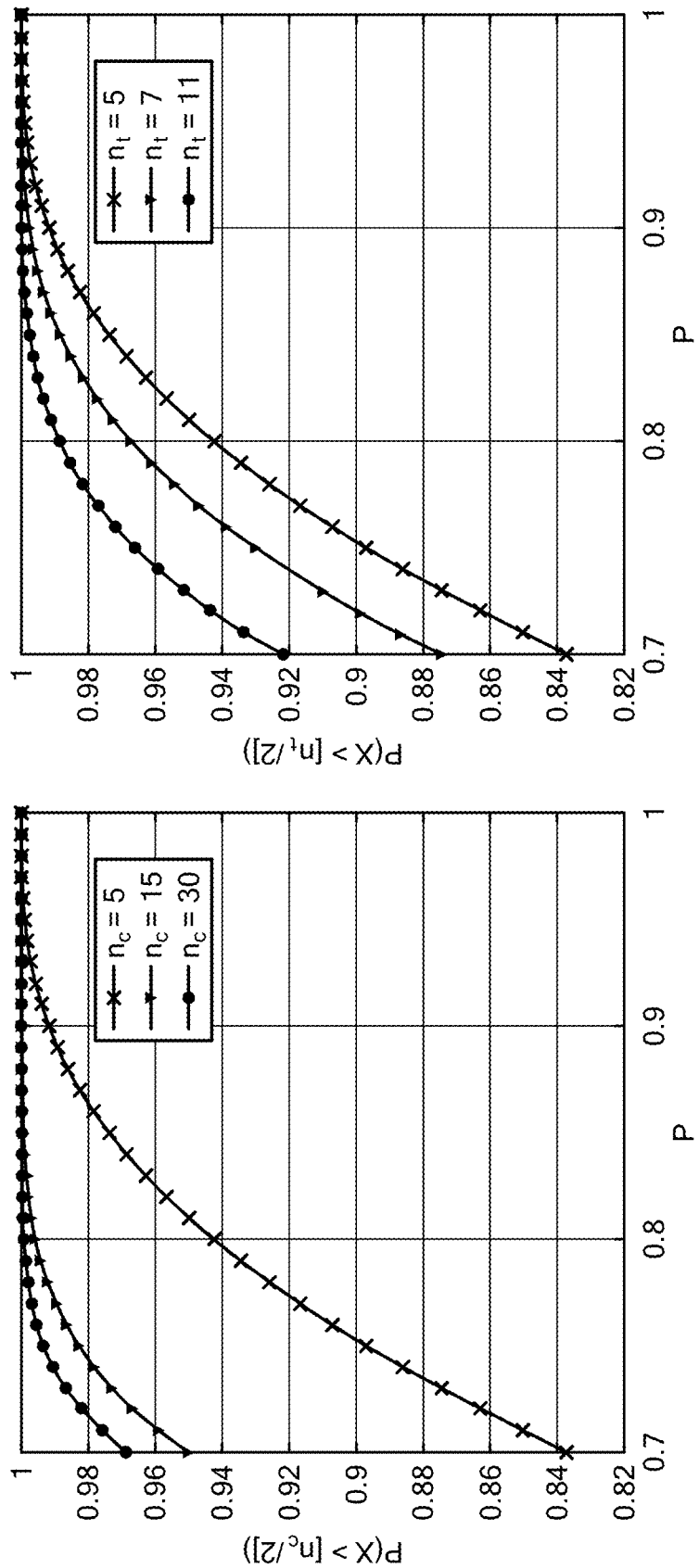
FIG. 8 illustrates graphs of the probability of successful classification when taking majority votes for varying CNN accuracy. The left figure illustrate majority vote taken among iEEG channels in one interval. The right figure illustrates majority vote taken among intervals in one iEEG channel.

The left side of FIG. 8 plots equation (4) for different numbers of iEEG channels, $n_c$, and varying CNN accuracy per channel, $p$. It can be seen that with a 15 channel iEEG, such as in the utilized dataset, a CNN accuracy of 70% for a single channel classification can yield an interval accuracy of about 95%.

If independence across time is assumed, a similar model approximates the interval vote case, except instead of summing across $n_c$ channels, the CDF is summed across multiple time intervals for a single channel.

$$P\left(X > \left\lfloor \frac{n_t}{2} \right\rfloor\right) = \sum_{h=\lceil n_t/2 \rceil}^{n_t} \binom{n_t}{h} p^h (1-p)^{n_t-h}, \qquad (5)$$

where $n_t$ is the number of 4 second time intervals that are used for a majority vote and X is the number of successful classifications no longer out of $n_c$ channels in a single time interval but out of $n_t$ time intervals for a single iEEG channel.

As can be seen from the right graph in FIG. 8, which plots equation (5), the accuracy of the system gets boosted beyond the CNN accuracy the more time intervals that are taken into account for a majority vote. In both the channel and interval vote cases, boosting comes at the cost of latency as a final decision cannot be made until a collection of CNN decisions have been made.

IV. Experimental Results

The performance of the ENDL system was experimentally evaluated. In Section IV-A, an implementation of a prototype is described. Section IV-B describes the testing of the prediction accuracy of the CNN in different scenarios. In Section IV-C, three end-to-end tasks are defined to compare the performance of the FPGA-based approach with a CPU and a cloud-based solution. In the same Section, a system-wide demonstration of ENDL is presented to measure latency, power, and energy consumption.

A. Prototype Implementation

A prototype of the system was implemented on a Zynq-7000 system-on-chip (SoC) on top of a Zedboard evaluation board. An SoC was chosen since (i) it is ideal to prototype systems having mixed FPGA and CPU components, and (ii) it possesses the right tradeoff between size, memory, and processing capabilities. The board features an FPGA that can be fabricated in a format as small as 1.7×1.7×0.8 cm. The prototype was implemented according to the model formulated in Section II. As reported in Section IV-C, the ENDL bitrate over the ultrasonic link was $R_{tx}$=150 k/bits (with a BER of $10^{-6}$). Thus, 150 kbit/s was the maximum application rate $R_{app}$ that could be satisfied. The processing delay introduced by the communication unit before transmission was $t_{proc}$=151 µs per packet. The DL module carried out a complete classification in $t_{DL}$=2.7 ms·15=40 ms (for the 2.7 ms see Table II; 15 is the number of channels). The result of the CNN was encoded into $B_{DL}$=2 bits, as three possible cases needed to be encoded: no seizure, partial seizure, general seizure. To fill a packet of $B_{pkt}$=16 bits, $N_c$=8 complete classifications were needed, which took approximately $T_{DL}=t_{DL}\cdot N_c$=324 ms to process the input by the CNN. To execute 8 classifications over all the channels, the DL took in input $M_{DL}$=1024·15·8·32=3.9 M bits. $T_{DL}$, is the maximum application time that the ENDL system can support. The condition $R_{DL}<R_{tx}$ was seamlessly respected, because $R_{DL}$=0.05 kbit/s. As for the sensor data, $R_{sens}=N_s\cdot r_{sens}$=15·250 kS/s (kilosample/sec)—that already included $t_{conv}$. The ADC had a resolution of η=32 bits, thus the conversion frequency of the ADC was $R_{conv}$=250·15·32=120 kbit/s. Condition III was also met, as the DL module read bits at rate $R_{DL,in}=M_{DL}/T_{DL}$=12 Mbit/s, which was $>R_{conv}$. Finally, the FIFO to avoid overflows was calculated to be at least $B_{pkt}\cdot K_{pkt}$=16 bits. The CNN itself had been trained and tested on a local computer. The weights and architecture of the CNN were then transferred to the FPGA. Thus, note that the CNN was not trained on the FPGA, but only used on the FPGA for predicting new outputs from new inputs once already trained offline. The weights and architecture of the CNN were first coded in C++ and then synthesized and packaged as a Verilog module using High Level Synthesis (HLS). The module was then integrated into a block design of the FPGA like any other module.

B. CNN Testing

Table I shows the classification accuracy obtained on the iEEG dataset with the models. Also evaluated were the effects of boosting by grouping the pre-seizure or non-seizure training samples into different sizes based on either the number of channels in the iEEG or the decision window. Then, the system mad a final decision on a group based on the majority classification within the group.

Channel Vote: to test taking a channel vote, the samples were in groups of 15 for the first patient and 24 for the second patient, which corresponded with the number of channels in the iEEG for each.

Interval Vote: to test the interval vote, the samples were grouped into 8 representing the 8 intervals of samples for a decision window in a single channel which corresponded to $N_c$ (not to be confused with $n_c$, number of IEEG channels).

The CNN was trained and tested utilizing (i) only Patient 1 data, (ii) only Patient 2 data, and (iii) a mixed dataset from the two patients. Using Patient 1 data (i) achieved an accuracy of 84% on the validation set and 82% on the test set. Using Patient 2 data (ii) achieved an accuracy of 66% on the validation set and 60% on the test set. Using the mixed dataset (iii) achieved an accuracy of 73% on the validation set and 82% on the test set. Within the test set it correctly classified 83% of the first patient's data and 73% of the second patient's data. Table I summarizes the resulting accuracy of taking a majority vote among multiple channels or among multiple intervals. It can be seen that in all cases taking a vote helped mitigate the low classification accuracy of the CNN alone. Also, the CNN's ability to classify the first patient's data did not improve greatly with the addition of the second patient's data; however the same was not true for the second patient. This implies that a personalized dataset is not enough to create an accurate model for a single patient.

TABLE I

Classification accuracy of CNN trained on various data sets:

| Scenario | Single Channel | Channel Vote | Interval Vote |
|---|---|---|---|
| Train/Test Patient 1 | 82% | 100% | 98% |
| Train/Test Patient 2 | 60% | 70% | 66% |
| Patient 1 on Mixed CNN | 83% | 100% | 98% |
| Patient 2 on Mixed CNN | 73% | 89% | 85% |

C. ENDL End-to-End Performance Evaluation

To further evaluate the performance of ENDL and compare it with a CPU-based and cloud-based approach, three different end-to-end tasks were defined, each encompassing the CNN execution, some processing, an ultrasonic data link, and communication with a cloud.

Figure 9:
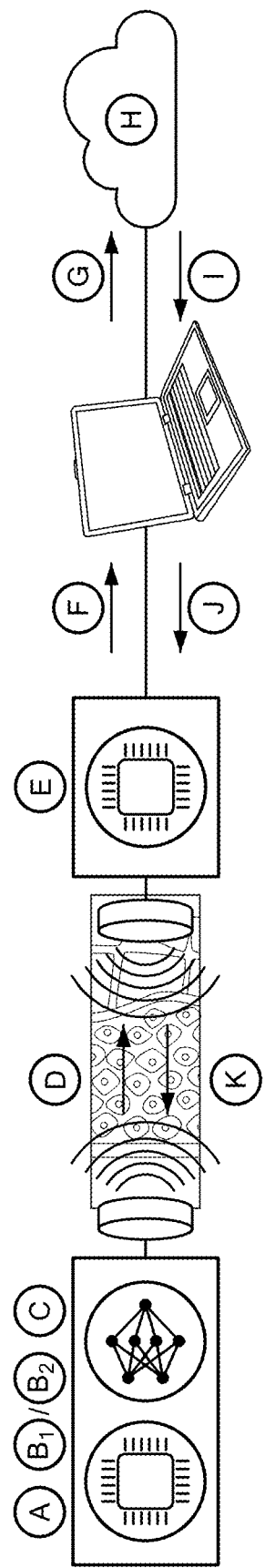
FIG. 9 is a schematic illustration of a model for task definitions: (A) processing; ($B_1$) FPGA deep learning; ($B_2$) CPU deep learning; (C) and (E) data processing; (D) and (K) ultrasonic link; (F) and (J) Ethernet IGigE; (G) and (I) TCP transfer; (H) cloud deep learning.

The block schematic illustrated in FIG. 9 was used as a general model in which ENDL was ultimately connected to a cloud system, outlining three possible IoIMT applications. Specifically, the following three tasks were defined:

Task 1—FPGA, an FPGA-based approach where the CNN classification was executed on the FPGA and the results (2 bytes worth of data) were sent to the cloud afterwards. The order of subtasks was A-$B_1$-C-D-E-F-G;

Task 2—CPU, a CPU-based approach that performed the DL algorithm on the implanted CPU and transferred the results to the cloud. The order of subtasks was A-$B_2$-C-D-E-F-G; and Task 3—Cloud, where the sensor measurements were sent directly to the cloud that hosted the CNN, processed the data and sent the results back to the ENDL system. The order of subtasks was A-C-D-E-F-G-H-I-J-K.

Figure 10:
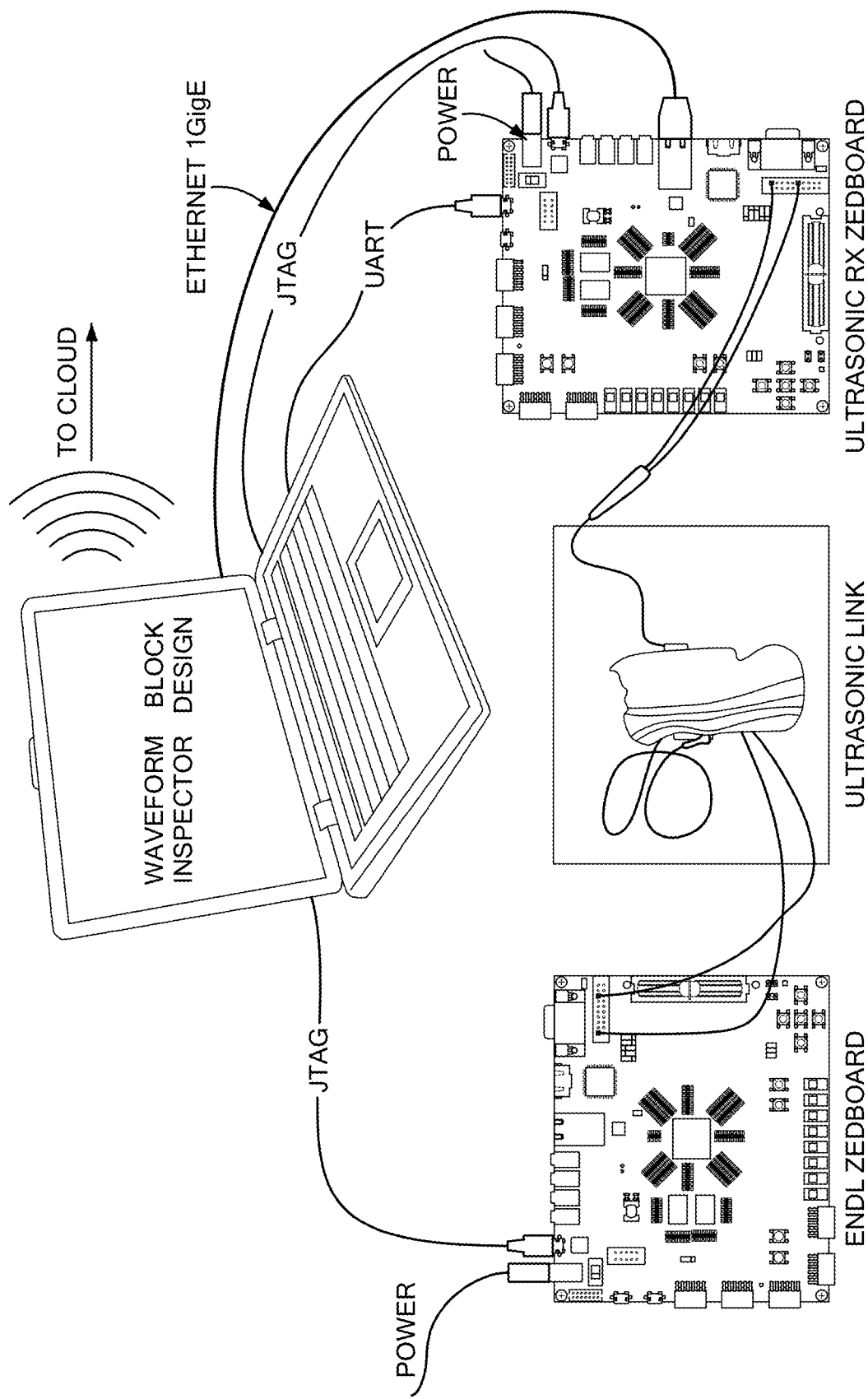
FIG. 10 is an illustration of an embedded networked deep learning testbed.

To measure the latency and energy consumption of each component of the tasks defined above, a testbed was set up as shown in FIG. 10. The first Zedboard—indicated as "ENDL"-hosted the ENDL prototype implementation, while the other Zedboard (which included an ultrasonic and a 1 GigE Ethernet interface) was connected to a host that exchanged data with the cloud. A 4 cm-thick pork belly composed of multiple layers (skin, fat, etc.) was used to imitate the ultrasound propagation in human tissue. The two ultrasonic transducers were attached to the porcine meat through a layer of aqueous gel, which was spread at the interface to attenuate the acoustic mismatch between the transducers and the tissue.

(1) CNN Latency. To compute the energy consumption of the learning tasks, first the latency to execute the learning task on the FPGA and on the Zedboard's CPU was computed. For this reason, the latency to perform a classification on one input (i.e., one sample interval for a single channel) on varying CNNs with randomized parameters in the FPGA was reported, where it was compared against the same CNN architecture implemented on the board's CPU. The reported CPU latency was averaged over 1000 measurements. The FPGA latency was measured through a timer implemented inside the FPGA. Table II shows that the latency of the FPGA-based solution was of one order of magnitude smaller than a CNN implemented on the CPU, independent of the type of CNN, which ultimately demonstrates the advantages of an FPGA-based implementation vs. a CPU one.

TABLE II

Latency measurements for a single classification on one input for varying CNN with varying parameters.

| # of CNN Parameters | CPU Latency [ms] | FPGA Latency [ms] |
| --- | --- | --- |
| 1772 | 51 | 1.8 |
| 6642 | 62 | 2.1 |
| 12424 (Prototype) | 71 | 2.7 |
| 17035 | 120 | 4.2 |

Figure 11:
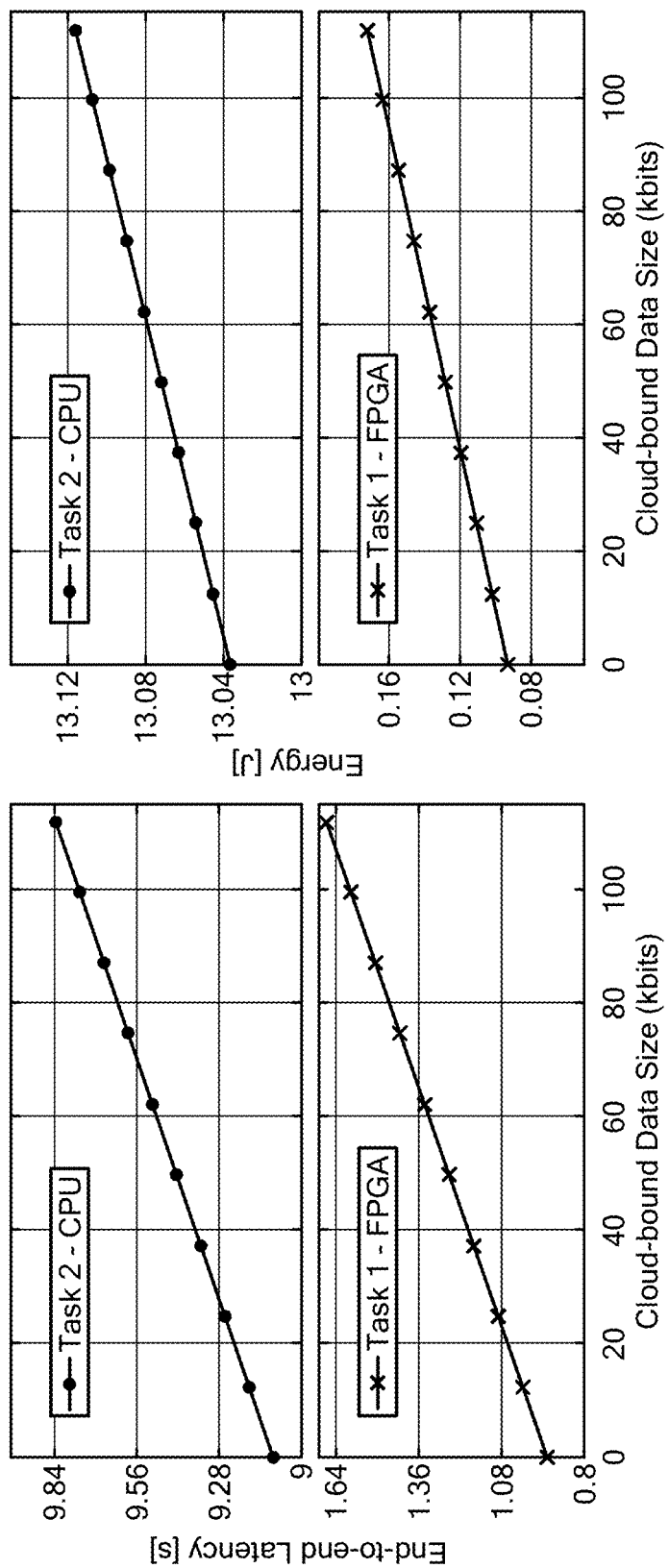
FIG. 11 illustrates graphs of end-to-end latency (left) and implant energy consumption (right) for varying the cloud-bound data size and a single execution for two tasks.

(2) Ultrasonic Link Latency. The next step was to measure the ultrasonic data rate—to estimate the time needed to transfer the CNN input data to the cloud. A bitrate of 150 kbits with a BER of $10^{-6}$ was measured for the ultrasonic connection and an average rate of 500 Mbit/s on the 1 GigE Ethernet link. The average uplink and downlink times to exchange data with the cloud, for packets smaller than 2 megabytes, were 232 ms and 142 ms, respectively. Both the Ethernet and the connection with the cloud were based on TCP transport protocol and used a socket to establish a connection. Each socket set-up time was measured to be approximately 96 ms. In a more general case, the amount of data that has to be sent to the cloud may be larger than 2 bytes (to include other information or to increase redundancy); therefore, the impact on latency and energy of the amount of data was examined. FIG. 11 shows the increase of the end-to-end delay and of the energy depending on the size of the cloud-bound data. This was calculated only for Task 1—FPGA and Task 2—CPU, because for Task 3—Cloud, the implant only needed to transfer the raw sensor data.

Figure 12:
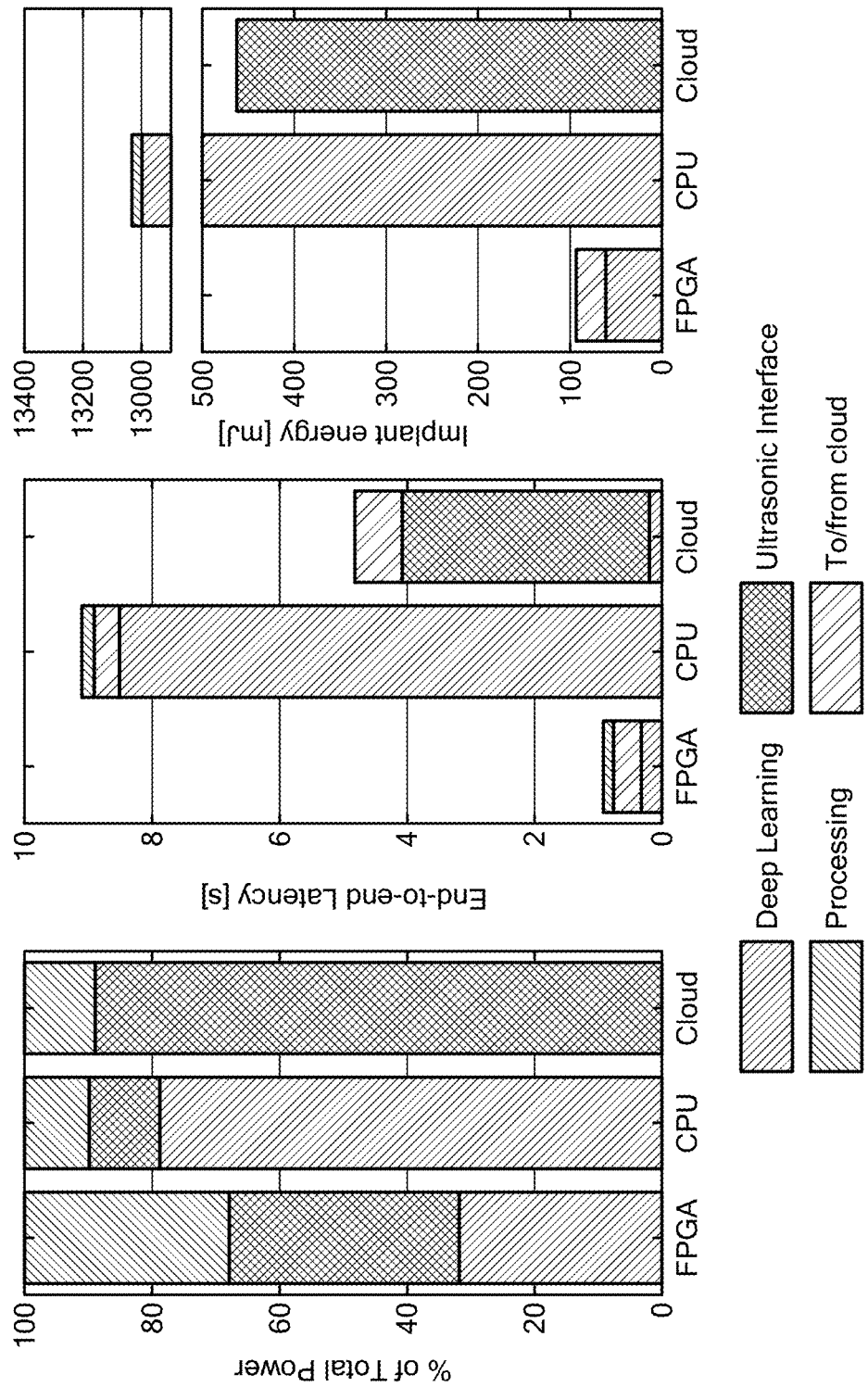
FIG. 12 illustrates graphs of power, latency, and energy consumption of three end-to-end tasks.

(3) End-to-End Performance. The latency information alone was not sufficient to have a complete insight of the task performance; therefore the power consumption of each subtask executed inside the SoC was measured using the Vivado tool provided by Xilinx, which gave a circuit-level breakdown of the power consumption on both the CPU and the FPGA of the SoC. Based on the measurements, the power, latency, and energy consumption of each task are reported in FIG. 12. The histograms show the distribution of the power between DL, external communications (Ethernet and to/from cloud), ultrasonic link and other operations performed on the implant, for each task. Notice that the total energy consumption required by Task 2—CPU was the highest. This was due to its slow CNN execution, lasting for about 9 s and the very high power consumption of the CPU (1.53 W total), which led to the largest energy consumption of 13.037 J. Notice that the high CNN execution time was due to (i) the slow CPU clock speed (667 MHz) as compared to the cloud-based implementation and (ii) consideration of the boosted model, which further increased latency (and thus energy consumption). Furthermore, Task 3—Cloud required the smallest amount of total power (0.57 W); however, it required more than 4 s for data communication, 80% of which (3.87 s) was needed to transfer data from/to the implant to/from the external unit over the ultrasonic link.

Conversely, Task 1—FPGA had an even distribution of the power (0.56 W total) between DL, ultrasonic communication and other operations. Indeed, since the data that needed to be transmitted outside were only the CNN classification results (i.e., 2 bytes), the time spent during ultrasonic communication was smaller than 1% of the total end-to-end delay. The latency histogram relative to Task 1—FPGA shows that 424 ms of the total 924 ms were spent to send data to the cloud. Note that there is minimum delay of 232 ms to upload a packet of any size smaller than 2 MB to the cloud. This fixed delay does not depend on the ENDL system and it does not impact the power (and the energy) consumption of the implant.

Figure 13:
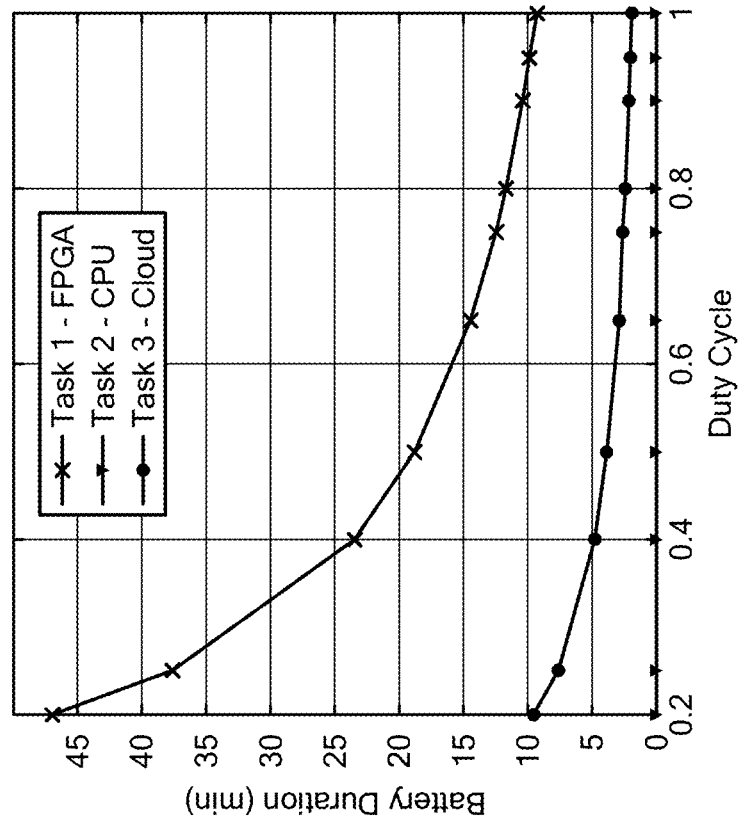
FIG. 13 illustrates graphs of rechargeable battery duration for varying duty cycle relative to the CNN execution time on the FPGA.
Figure 13:
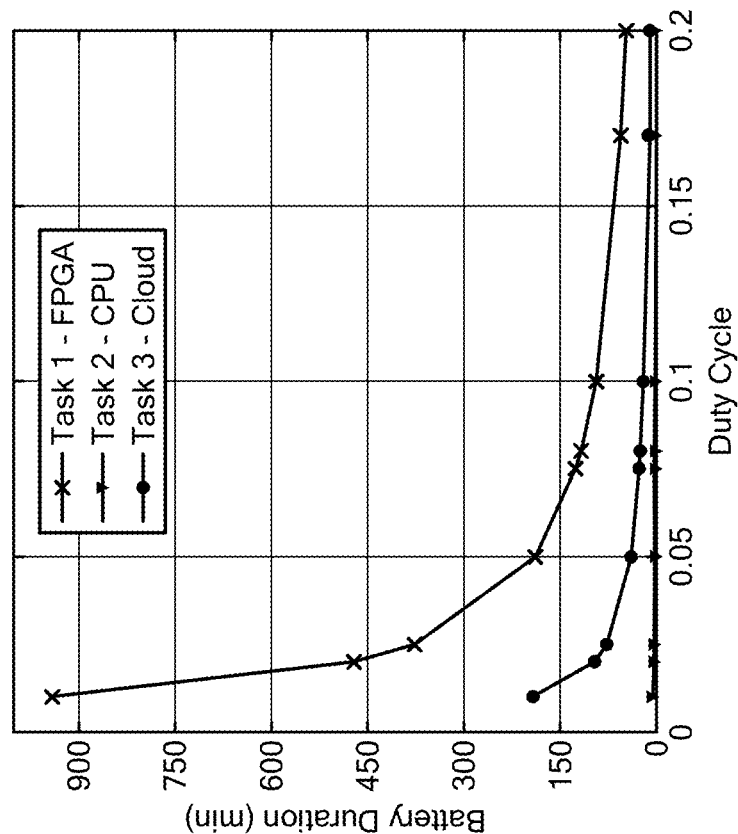

(4) Lifetime. To have a practical understanding of the experimental results and their impact on the lifetime of the platform, consider the case in which the CNN is executed at periodic intervals. The energy consumption of Task 1—FPGA was compared with Task 2—CPU and Task 3—Cloud using a 12 mAh rechargeable battery (PowerStream GM300910) as a reference to power the implant. A duty cycle was defined as the fraction of the time to execute the CNN (ON time) on the FPGA. FIG. 13 shows the duration of the battery for different values of the duty cycle assuming energy consumption values measured above for each task. FIG. 13 shows that the battery duration of the platform was about 10× longer than the cloud-based implementation.

Figure 14:
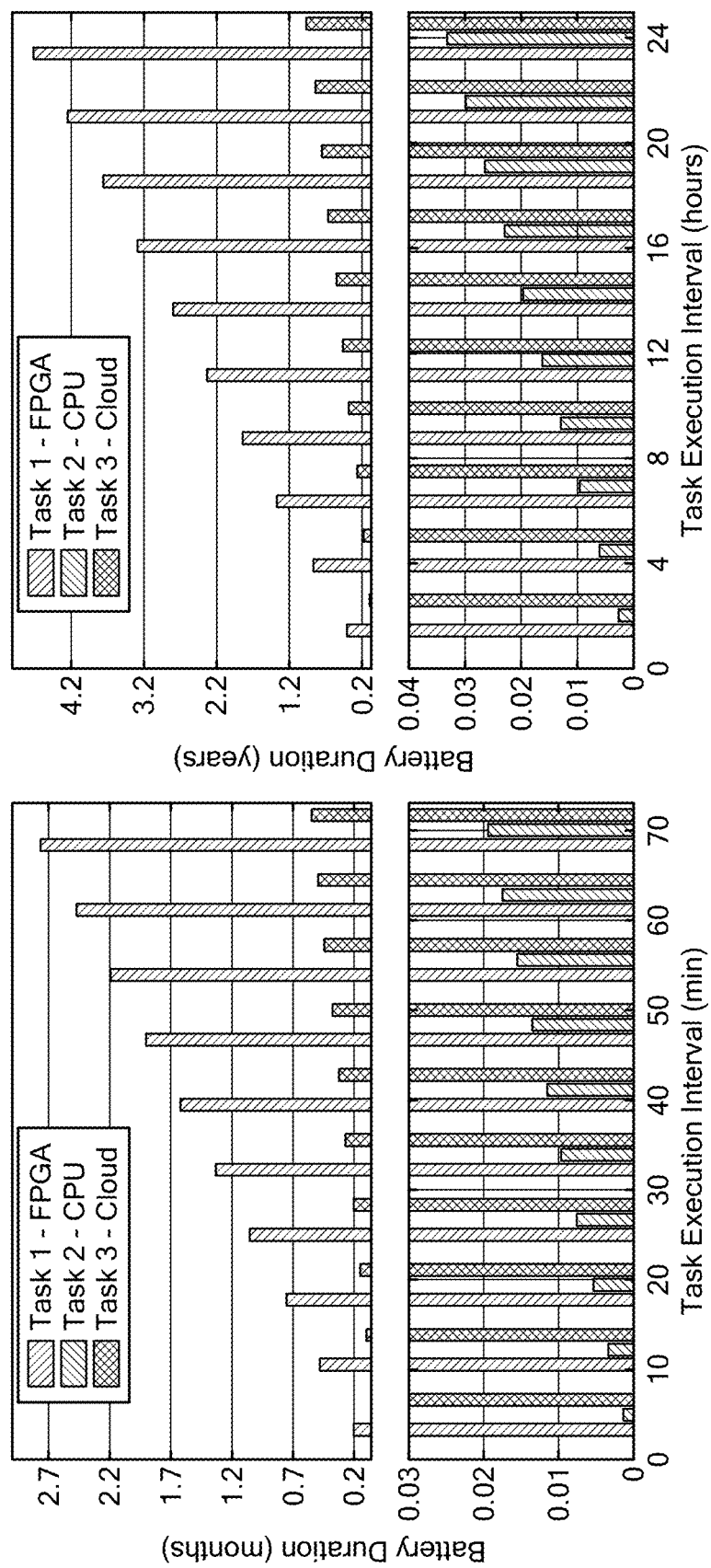
FIG. 14 illustrates graphs of rechargeable battery duration for varying task execution intervals over a long term perspective.

To further investigate this aspect, FIG. 14 shows the battery duration in long-term applications where the CNN was executed from every few minutes to one time per day. When the DL algorithm was executed every few minutes the battery lasted from a week to almost three months in the case of FPGA, but only up to 16 days for Task 3—Cloud and barely 13 hours for Task 2—CPU. By increasing the execution interval, the FPGA-based task can lead to a battery lifetime varying from few months up to almost 5 years, whereas the CPU-based task drains the battery in less than a year in any case.

As used herein, "consisting essentially of" allows the inclusion of materials or steps that do not materially affect the basic and novel characteristics of the claim. Any recitation herein of the term "comprising," particularly in a description of components of a composition or in a description of elements of a device, can be exchanged with "consisting essentially of" or "consisting of"

The present technology has been described in conjunction with certain preferred embodiments and aspects. It is to be understood that the technology is not limited to the exact details of construction, operation, exact materials or embodiments or aspects shown and described, and that various modifications, substitution of equivalents, alterations to the compositions, and other changes to the embodiments and aspects disclosed herein will be apparent to one of skill in the art.

What is claimed is:

1. A deep learning medical device implantable in a body, comprising:
a sensing and actuation unit comprising one or more implantable sensors operative to sense physiological parameters of the body and one or more actuators; and
a processing and communication unit, in communication with the sensing and actuation unit, comprising:
a deep learning module operative to receive input samples from the sensing and actuation unit, the deep learning module including a neural network trained to process the input samples through a plurality of layers to classify the physiological parameters sensed by the sensing and actuation unit and provide classification results, wherein the input samples are provided as a plurality of channels, and the deep learning module is operative to predict classifications for each channel of the plurality of channels individually per a sampling time interval and at least one of:
select a spatial probable class output across space by a spatial majority vote across the plurality of channels by determining a probability that a number of successful spatially predicted classifications is at least greater than half of a number of the plurality of channels within the sampling time interval according to a spatial class output cumulative distribution function (spatial CDF):

$$P\left(X > \left\lfloor \frac{n_c}{2} \right\rfloor\right) = 1 - F_X\left(\left\lfloor \frac{n_c}{2} \right\rfloor\right)$$
$$= 1 - \sum_{h=0}^{\lfloor n_c/2 \rfloor} \binom{n_c}{h} p^h (1-p)^{n_c-h}$$
$$= \sum_{h=\lceil n_c/2 \rceil}^{n_c} \binom{n_c}{h} p^h (1-p)^{n_c-h}$$

wherein X is the number of successful spatially predicted classifications within the sampling time interval, wherein $n_c$ is a total number of channels in the plurality of channels used for the majority vote, wherein p is a probability of success of the neural network for a single one of the plurality of channels, and wherein $$\left\lceil \frac{n_c}{2} \right\rceil$$

is a ceiling of $$\frac{n_c}{2};$$

and/or
select a temporal probable class output across time by a temporal majority vote across a plurality of the sampling time intervals within each individual one of the plurality of channels by determining a probability that a number of successful temporally predicted classifications is at least greater than half of the number of sampling time intervals within the individual one of the plurality of channels according to a temporal class output cumulative distribution function (temporal CDF):

$$P\left(X > \left\lfloor \frac{n_t}{2} \right\rfloor\right) = \sum_{h=\lceil n_t/2 \rceil}^{n_t} \binom{n_t}{h} p^h (1-p)^{n_t-h}$$

wherein X is the number of successful temporally predicted classifications within the individual one of the plurality of channels, wherein $n_t$ is a total number of sampling time intervals used for the majority vote, wherein p is the probability of success of the neural network for each individual one of the sampling time intervals, anD wherein $$\left\lceil \frac{n_c}{2} \right\rceil$$

is a ceiling of $$\frac{n_t}{2},$$

and
a communication interface in communication with the deep learning module to receive the classification results, the communication interface comprising an ultrasonic transceiver to transmit and receive ultrasonic signals through biological tissue.

2. The device of claim 1, wherein the processing and communication unit comprises one or more logic devices and the deep learning module is implemented in circuitry of the one or more logic devices, and/or the processing and communication unit comprises one or more processors, and the deep learning module is implemented on the one or more processors.

3. The device of claim 1, wherein the processing and communication unit includes memory disposed to buffer transmissions of the input samples from the sensing and actuation unit to the deep learning module, and/or memory disposed to buffer transmissions of the classification results from the deep learning module to the communication interface.

4. The device of claim 1, wherein the deep learning module is operative to receive the input samples from the sensing and actuating unit at a rate equal to or greater than an output rate of the sensing and actuating unit, wherein the output rate of the sensing and actuating unit is a rate of conversion of analog signals from the one or the plurality of sensors into digital samples indicative of the physiological parameters.

5. The device of claim 1, wherein the deep learning module is operative to produce the classification results encoded with a number of bits within a total time that is equal to or less than a time requested by a medical or health application, wherein the total time is determined by a processing latency time to compute a single classification by the deep learning module multiplied by a number of classification cycles.

6. The device of claim 1, wherein the deep learning module is operative to produce the classification results at a rate that is less than a transmission rate of the communication interface and equal to or greater than a rate determined by a medical or health application.

7. The device of claim 1, wherein the neural network of the learning module comprises a convolutional neural network comprising a plurality of layers, each layer comprising one or more one-dimensional arrays.

8. The device of claim 1, wherein the plurality of layers of the neural network comprises an input layer, an output layer, and one or more hidden layers, and wherein each layer of the plurality of layers is configured with one or more of an activation function, weight, filter, or bias.

9. The device of claim 1, wherein the neural network comprises a convolutional neural network and the plurality of layers includes one or more of a convolution layer, a dense layer, a fully-connected layer, a rectified linear layer, and a pooling layer.

10. The device of claim 1, wherein the neural network of the deep learning module is trained with data provided as a plurality of channels down-sampled to provide a plurality of one-dimensional arrays each representing samples from one of the plurality of channels.

11. The device of claim 1, wherein the communication interface is operative to transfer data to an external device at an average data rate measured in bits per second that is equal to or greater than an average data rate of data determined by a medical or health application, and wherein the sensing and actuation unit is configured to carry out instructions based on the medical or health application.

12. The device of claim 1, wherein the communication interface includes a temporary memory storage operative to store bits produced by the learning module until a payload of one or more packets can be filled with the bits for transmission.

13. The device of claim 12, wherein the temporary memory storage has a minimum size of at least a number of bits per packet $B_{pkt}$ multiplied by a number of packets $K_{pkt}$ and/or the temporary memory storage comprises a first in first out storage device.

14. The device of claim 1, wherein the communication interface has a data transmission rate $R_{tx}$ greater than an average rate $R_{DL}$ of bits produced by the learning module.

15. The device of claim 1, wherein the sensing and actuation unit comprises one or a plurality of analog sensors of one or more physiological parameters and an analog to digital converter operative to convert analog signals from the at least one analog sensor indicative of the one or more physiological parameters into digital samples for transmission to the processing and communication unit.

16. The device of claim 15, wherein the sensing and actuation unit is operative to convert the analog signals into the digital samples at a conversion rate $R_{conv}$ determined by a number $N_s$ of the analog sensors, an average number of voltage values $\bar{r}_{sens}$ transmitted by the one or the plurality of analog sensors, a conversion resolution $\eta$ of the analog to digital converter, and a latency $t_{conv}$ of the analog to digital converter for a single sample.

17. The device of claim 15, further comprising a temporary storage buffer in communication with the sensing and actuating unit to temporarily store the input samples received from the sensing and actuating unit, the temporary storage buffer comprising storage for at least a minimum number of bits that can be processed by the deep learning module before the sensing and actuation unit terminates conversion of the analog signals into the digital samples.

18. A method of sensing and classifying physiological parameters of a body, comprising:
(a) implanting a deep learning medical device into the body, the deep learning medical device comprising:
  a sensing and actuation unit comprising one or more implantable sensors operative to sense physiological parameters of the body and one or more actuators; and
  a processing and communication unit, in communication with the sensing and actuation unit, comprising:
    a deep learning module operative to receive input samples from the sensing and actuation unit, the deep learning module including a neural network trained to process the input samples through a plurality of layers to classify the physiological parameters sensed by the sensing and actuation unit and provide classification results, wherein the input samples are provided as a plurality of channels, and
    a communication interface in communication with the deep learning module to receive the classification results, the communication interface comprising an ultrasonic transceiver to transmit and receive ultrasonic signals through biological tissue;
(b) transmitting the input samples from the sensing and actuating unit to the communication and processing unit as the plurality of channels;
(c) predicting, by the deep learning module, classifications for each of the p a channels individually per a sampling time interval;
(d) at least one of:
  selecting a spatial probable class output across space by a spatial majority vote across the plurality of channels by determining a probability that a number of successful spatially predicted classifications is at least greater than half of a number of the plurality of channels within the sampling time interval according to a spatial class output cumulative distribution function (spatial CDF)

$$P\left(X > \left\lfloor \frac{n_c}{2} \right\rfloor\right) = 1 - F_X\left(\left\lfloor \frac{n_c}{2} \right\rfloor\right)$$
$$= 1 - \sum_{h=0}^{\lfloor n_c/2 \rfloor} \binom{n_c}{h} p^h (1-p)^{n_c-h}$$
$$= \sum_{h=\lceil n_c/2 \rceil}^{n_c} \binom{n_c}{h} p^h (1-p)^{n_c-h}$$

wherein X is the number of successful spatially predicted classifications within the sampling time interval, wherein $n_c$ is a total number of channels in the plurality of channels used for the majority vote, wherein p is a probability of success of the neural network for a single one of the plurality of channels, and wherein $\lceil n_c/2 \rceil$ is a ceiling of $n_c/2$; and/or
  selecting a temporal probable class output across time by a temporal majority vote across a plurality of the sampling time intervals within each individual one of the plurality of channels by determining a probability that a number of successful temporally predicted classifications is at least greater than half of the number of sampling time intervals within the individual one of the plurality of channels according to a temporal class output cumulative distribution function (temporal CDF)

$$P\left(X > \left\lfloor \frac{n_t}{2} \right\rfloor\right) = \sum_{h=\lceil n_t/2 \rceil}^{n_t} \binom{n_t}{h} p^h (1-p)^{n_t-h}$$

wherein X is the number of successful temporally predicted classifications within the individual one of the plurality of channels wherein $n_t$ is a total number of sampling time intervals used for the majority vote, wherein p is the probability of success of the neural network for each individual one of the sampling time intervals, and wherein $$\left\lceil \frac{n_c}{2} \right\rceil$$

is a ceiling of $$\frac{n_c}{2};$$

and
(e) one or both of:
  at the communication interface, transmitting the classification results to an external device, and
  at the processing and communication unit, determining instructions, based on the classification results, for the sensing and actuation unit and transmitting the instructions to the sensing and actuation unit.

19. A method of embedding deep learning into an implantable medical device, comprising:
  (a) training a deep learning module including a neural network having a plurality of layers with a set of physiological data; and
  (b) providing the implantable medical device comprising:
    a sensing and actuation unit comprising one or more implantable sensors operative to sense physiological parameters of a body and one or more actuators; and
    a processing and communication unit, in communication with the sensing and actuation unit, comprising:
    the deep learning module trained in step (a) and operative to receive input samples from the sensing and actuation unit, the deep learning module including a neural network trained to process the input samples through a plurality of layers to classify the physiological parameters sensed by the sensing and actuation unit and provide classification results, wherein the input samples are provided as a plurality of channels, and
    a communication interface in communication with the deep learning module to receive the classification results, the communication interface comprising an ultrasonic transceiver to transmit and receive ultrasonic signals through biological tissue;
  (c) predicting, by the deep learning module, classifications for each channel of the plurality of channels individually per a sampling time interval; and
  (d) at least one of:
    selecting a spatial probable class output across space by a spatial majority vote across the plurality of channels by determining a probability that a number of successful spatially predicted classifications is at least greater than half of a number of the plurality of channels within the sampling time interval according to a spatial class output cumulative distribution function (spatial CDF)

$$P\left(X > \left\lfloor \frac{n_c}{2} \right\rfloor\right) = 1 - F_X\left(\left\lfloor \frac{n_c}{2} \right\rfloor\right)$$
$$= 1 - \sum_{h=0}^{\lfloor n_c/2 \rfloor} \binom{n_c}{h} p^h (1-p)^{n_c-h}$$
$$= \sum_{h=\lceil n_c/2 \rceil}^{n_c} \binom{n_c}{h} p^h (1-p)^{n_c-h}$$

wherein X is the number of successful spatially predicted classifications within the sampling time interval, wherein $n_c$ is a total number of channels in the plurality of channels used for the majority vote, wherein p is a probability of success of the neural network for a single one of the plurality of channels, and wherein $\lceil n_c/2 \rceil$ is a ceiling of $n_c/2$; and/or selecting a temporal probable class output across time by a temporal majority vote across a plurality of the sampling time intervals within each individual one of the plurality of channels by determining a probability that a number of successful temporally predicted classifications is at least greater than half of the number of sampling time intervals within the individual one of the plurality of channels according to a temporal class output cumulative distribution function (temporal CDF)

$$P\left(X > \left\lfloor \frac{n_t}{2} \right\rfloor\right) = \sum_{h=\lceil n_t/2 \rceil}^{n_t} \binom{n_t}{h} p^h (1-p)^{n_t-h}$$

wherein X is the number of successful temporally predicted classifications within the individual one of the plurality of channels, wherein $n_t$ is a total number of sampling time intervals used for the majority vote, wherein p is the probability of success of the neural network for each individual one of the sampling time intervals, and wherein $$\left\lceil \frac{n_t}{2} \right\rceil$$

is a ceiling of $$\frac{n_t}{2}.$$

* * * * *